(12) United States Patent
Mihara et al.

(10) Patent No.: US 12,256,736 B2
(45) Date of Patent: Mar. 25, 2025

(54) PYRIDAZINE COMPOUND AND HERBICIDE

(71) Applicant: Nippon Soda Co., Ltd., Tokyo (JP)

(72) Inventors: Ken Mihara, Odawara (JP); Yoji Ikeda, Odawara (JP); Yukina Taki, Odawara (JP); Kazushige Kato, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 701 days.

(21) Appl. No.: 17/636,701

(22) PCT Filed: Sep. 23, 2020

(86) PCT No.: PCT/JP2020/035682
§ 371 (c)(1),
(2) Date: Feb. 18, 2022

(87) PCT Pub. No.: WO2021/060236
PCT Pub. Date: Apr. 1, 2021

(65) Prior Publication Data
US 2022/0287305 A1   Sep. 15, 2022

(30) Foreign Application Priority Data

Sep. 25, 2019   (JP) .................................. 2019-174532

(51) Int. Cl.
| C07D 409/04 | (2006.01) |
| A01N 43/58 | (2006.01) |
| A01P 13/00 | (2006.01) |
| C07D 407/04 | (2006.01) |

(52) U.S. Cl.
CPC .............. *A01N 43/58* (2013.01); *A01P 13/00* (2021.08); *C07D 409/04* (2013.01)

(58) Field of Classification Search
CPC ............................ C07D 407/04; C07D 409/04
See application file for complete search history.

(56) References Cited

U.S. PATENT DOCUMENTS

| 5,723,411 A | 3/1998 | Stevenson |
| 9,693,556 B2 * | 7/2017 | Bhonoah .............. C07D 409/14 |
| 2009/0111696 A1 | 4/2009 | Kiji et al. |
| 2013/0281299 A1 | 10/2013 | Kuragano et al. |
| 2014/0256546 A1 | 9/2014 | Bhonoah et al. |
| 2017/0050953 A1 | 2/2017 | Selby et al. |

FOREIGN PATENT DOCUMENTS

| CN | 103874688 B | 6/2014 |
| EA | 201692186 A1 | 4/2017 |
| JP | 2004-043397 A | 2/2004 |
| JP | 2014-528960 A | 10/2014 |
| JP | 2018-533577 A | 11/2018 |
| TW | I375669 B | 11/2012 |
| TW | I507132 B | 11/2015 |
| WO | WO-88/04652 A1 | 6/1988 |

(Continued)

OTHER PUBLICATIONS

PubChem CID 57568400, National Center for Biotechnology Information. PubChem Compound Summary for CID 57568400, 5-(1-Benzothiophen-4-yl)-4-methoxy-2-propan-2-ylpyridazin-3-one. https://pubchem.ncbi.nlm.nih.gov/compound/57568400. Accessed Jan. 28, 2025, create date Aug. 19, 2012. (Year: 2012).*
PubChem CID 57568387, National Center for Biotechnology Information. PubChem Compound Summary for CID 57568387, 5-(1-Benzofuran-4-yl)-4-methoxy-2-propan-2-ylpyridazin-3-one. https://pubchem.ncbi.nlm.nih.gov/compound/57568387. Accessed Jan. 28, 2025, create date Aug. 19, 2012. (Year: 2012).*
Office Action dated Mar. 4, 2024 in TW 109132972, with English translation of search report.
Office Action dated Nov. 1, 2023 in RU 2022106218, with English translation.
International Search Report dated Nov. 24, 2020 in PCT/JP2020/035682, with English translation.
Office Action dated Feb. 19, 2024 in AP/P/2022/013870.

*Primary Examiner* — Laura L Stockton
(74) *Attorney, Agent, or Firm* — FITCH, EVEN, TABIN & FLANNERY, LLP

(57) ABSTRACT

A compound represented by formula (I) or a salt thereof, and a herbicide containing at least one selected from the group consisting of the compounds described above as an active ingredient. In formula (I), $R^1$ represents a substituted or unsubstituted C1 to C6 alkyl group, or the like, $R^2$ represents H, a substituted or unsubstituted C1 to C6 alkyl group, or the like, $R^3$ represents H, a substituted or unsubstituted C1 to C6 alkyl group, or the like, $R^4$ represents a halogeno group, a substituted or unsubstituted C1 to C6 alkyl group, or the like, $R^5$ represents H or a halogeno group, $R^6$ represents H or a halogeno group, A represents a substituted or unsubstituted C1 to C4 alkylene group, a substituted or unsubstituted C2 to C3 alkenylene group, or a C1 to C2 alkyleneoxy C1 to C2 alkylene group, $X^1$ represents O or a sulfonyl group, $X^2$ represents O, a sulfenyl group, or the like, m represents 0 or 1, n represents 0 or 1, and m+n=1 or 2, and when A is a substituted or unsubstituted methylene group, m+n=2.

[Chem. 1]

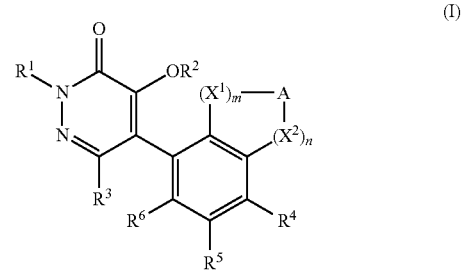

4 Claims, No Drawings

(56) References Cited

FOREIGN PATENT DOCUMENTS

| WO | WO-2013/050421 A1 | 4/2013 |
| WO | WO-2017/074988 A1 | 5/2017 |
| WO | WO-2017/074992 A1 | 5/2017 |

\* cited by examiner

PYRIDAZINE COMPOUND AND HERBICIDE

TECHNICAL FIELD

The present invention relates to a pyridazine compound and a herbicide containing the same as an active ingredient.

The present application claims priority on Japanese Patent Application No. 2019-174532, filed in Japan on Sep. 25, 2019, the content of which is incorporated herein by reference.

BACKGROUND ART

Herbicides may be used for controlling weeds in the cultivation of agricultural and horticultural crops. Heretofore, various compounds have been proposed as active ingredients of herbicides.

For example, Patent Document 1 discloses a pyridazine compound represented by formula (A) and the like.

[Chem. 1]

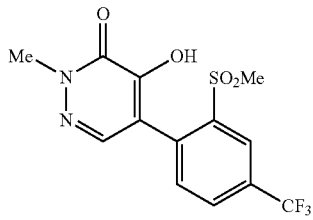

(A)

PRIOR ART LITERATURE

Patent Documents

Patent Document 1: WO 2013/050421

SUMMARY OF THE INVENTION

Problems to be Solved by the Invention

Herbicides are required not only to exhibit superior effects of controlling weeds, but also to have reduced phytotoxicity to crops, to be less likely to remain in the environment, and to cause no environmental pollution.

An object of the present invention is to provide a novel pyridazine compound useful as an active ingredient of herbicides which exhibits a reliable effect of controlling weeds even at a low dosage, has less phytotoxicity to crops, and is highly safe for the environment, and provide herbicides.

As a result of diligent studies in order to achieve the object mentioned above, the present invention containing the aspects described below has been completed.

[1] A compound represented by formula (I) or a salt thereof.

[Chem. 2]

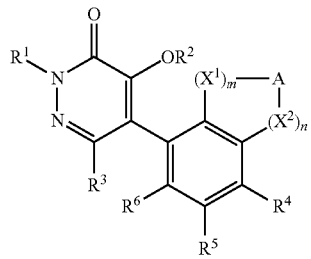

(I)

In formula (I), $R^1$ represents a substituted or unsubstituted C1 to C6 alkyl group, a substituted or unsubstituted C2 to C6 alkenyl group, a substituted or unsubstituted C2 to C6 alkynyl group, or a substituted or unsubstituted C3 to C6 cycloalkyl group, $R^2$ represents a hydrogen atom, a substituted or unsubstituted C1 to C6 alkyl group, a substituted or unsubstituted C2 to C6 alkenyl group, a substituted or unsubstituted C2 to C6 alkynyl group, a group represented by $R^a$—CO—, a group represented by $R^aO$—CO—, a group represented by $R^aNH$—CO—, a group represented by $R^a{}_2N$—CO—, a group represented by $R^a$—$SO_2$—, a group represented by $R^a$—CO—O—$CR^b{}_2$—, or a group represented by $R^aO$—CO—O—$CR^b{}_2$—, each $R^a$ independently represents a substituted or unsubstituted C1 to C6 alkyl group, a substituted or unsubstituted C2 to C6 alkenyl group, a substituted or unsubstituted C2 to C6 alkynyl group, a substituted or unsubstituted C3 to C6 cycloalkyl group, a substituted or unsubstituted phenyl group, a substituted or unsubstituted naphthyl group, or a substituted or unsubstituted 5- to 6-membered heterocyclyl group, each $R^b$ independently represents a hydrogen atom, or a substituted or unsubstituted C1 to C6 alkyl group, $R^3$ represents a hydrogen atom, a substituted or unsubstituted C1 to C6 alkyl group, a substituted or unsubstituted C2 to C6 alkenyl group, a substituted or unsubstituted C2 to C6 alkynyl group, or a substituted or unsubstituted C3 to C6 cycloalkyl group, $R^4$ represents a halogeno group, a substituted or unsubstituted C1 to C6 alkyl group, a substituted or unsubstituted C1 to C6 alkoxy group, a substituted or unsubstituted phenyl group, a substituted or unsubstituted naphthyl group, a substituted or unsubstituted 5- to 6-membered heteroaryl group, or a cyano group, $R^5$ represents a hydrogen atom, or a halogeno group, $R^6$ represents a hydrogen atom, or a halogeno group, A represents a substituted or unsubstituted C1 to C4 alkylene group, a substituted or unsubstituted C2 to C3 alkenylene group, or a substituted or unsubstituted C1 to C2 alkyleneoxy C1 to C2 alkylene group, $X^1$ represents an oxygen atom, or a sulfonyl group, $X^2$ represents an oxygen atom, a sulfenyl group, a sulfinyl group, a sulfonyl group, a group represented by —S(=$NR^c$)—, or a group represented by —S(=O)(=$NR^c$)—, each $R^c$ independently represents a hydrogen atom, a substituted or unsubstituted C1 to C6 alkyl group, a substituted or unsubstituted phenyl group, a substituted or unsubstituted naphthyl group, or a cyano group, m represents 0 or 1, n represents 0 or 1, and the sum of m and n is 1 or 2, and when A is a substituted or unsubstituted methylene group, the sum of m and n is 2.

[2] A herbicide containing at least one selected from the group consisting of the compounds as described in [1] mentioned above and salts thereof, as an active ingredient.

[3] A method for controlling weeds of monocotyledonous species and/or dicotyledonous species in useful plants, containing the step of applying the compound as described in [1] mentioned above or a salt thereof, or the herbicide including the compound mentioned above, to weeds mentioned above and/or plants mentioned above and/or locuses thereof.

Effects of the Invention

The pyridazine compounds of the present invention exhibit a reliable effect of controlling weeds even at a low dosage, have less phytotoxicity to crops, and are highly safe for the environment. For this reason the pyridazine compounds of the present invention are useful as an active ingredient of herbicides. The herbicides of the present invention can be safely used for controlling weeds in the cultivation of agricultural and horticultural crops.

Embodiments for Carrying Out the Invention

The pyridazine compound of the present invention (hereinafter also simply referred to as "compound of the present invention" in some cases) is a compound represented by formula (I) (hereafter also referred to as the compound (I) in some cases) or a salt of the compound (I). In compounds (I), hydrates, various solvates, crystal polymorphisms, and the like are also included. Compounds (I) may contain stereoisomers and tautomers based on an asymmetric carbon, a double bond and the like. Such isomers and a mixture thereof are included as a whole in the technical scope of the present invention.

In the present invention, the term "unsubstituted" means only the core group. When the term "substituted" does not appear and only the name of the core group is recorded, the meaning "unsubstituted" is implied unless specifically stated otherwise.

On the other hand, the term "substituted" means that one of the hydrogen atoms of the core group has been substituted with a group having a structure either the same as or different from the core group. Accordingly, the "substituent" is another group that is bonded to the core group. There may be either one substituent, or two or more substituents. In the case of two or more substituents being present, the substituents may be the same or different.

Terms such as "C1 to C6" indicate that the number of carbon atoms in the core group ranges from 1 to 6 or the like. This number of carbon atoms does not include the number of carbon atoms that exist within substituents. For example, in the case of a butyl group having an ethoxy group, this group is classified as a C2 alkoxy C4 alkyl group.

There are no particular limitations on the "substituent", as long as it is chemically permissible and yields a compound having the effects of the present invention.

Specific examples of groups that can be a "substituent" include the groups listed below.

C1 to C6 alkyl groups such as a methyl group, an ethyl group, an n-propyl group, an i-propyl group, an n-butyl group, an s-butyl group, an i-butyl group, a t-butyl group, an n-pentyl group, and an n-hexyl group;

C2 to C6 alkenyl groups such as a vinyl group, a 1-propenyl group, a 2-propenyl group (an allyl group), a 1-butenyl group, a 2-butenyl group, a 3-butenyl group, a 1-methyl-2-propenyl group, and a 2-methyl-2-propenyl group;

C2 to C6 alkynyl groups such as an ethynyl group, a 1-propynyl group, a 2-propynyl group, a 1-butynyl group, a 2-butynyl group, a 3-butynyl group, and a 1-methyl-2-propynyl group;

C3 to C6 cycloalkyl groups such as a cyclopropyl group, a cyclobutyl group, a cyclopentyl group, and a cyclohexyl group;

a phenyl group, a naphthyl group;

phenyl C1 to C6 alkyl groups such as a benzyl group, and a phenethyl group;

3- to 6-membered heterocyclyl groups;

3- to 6-membered heterocyclyl C1 to C6 alkyl groups;

a hydroxyl group;

C1 to C6 alkoxy groups such as a methoxy group, an ethoxy group, an n-propoxy group, an i-propoxy group, an n-butoxy group, an s-butoxy group, an i-butoxy group, and a t-butoxy group;

C2 to C6 alkenyloxy groups such as a vinyloxy group, an allyloxy group, a propenyloxy group, and a butenyloxy group;

C2 to C6 alkynyloxy groups such as an ethynyloxy group and a propargyloxy group;

a phenoxy group, a naphthoxy group;

phenyl C1 to 6 alkoxy groups such as a benzyloxy group, and a phenethyloxy group;

5- to 6-membered heteroaryloxy groups such as a thiazolyloxy group and a pyridyloxy group;

5- to 6-membered heteroaryl C1 to C6 alkyloxy groups such as a thiazolylmethyloxy group and a pyridylmethyloxy group;

a formyl group;

C1 to C6 alkylcarbonyl groups such as an acetyl group, and a propionyl group;

a formyloxy group;

C1 to C6 alkylcarbonyloxy groups such as an acetyloxy group, and a propionyloxy group;

a benzoyl group;

C1 to C6 alkoxycarbonyl groups such as a methoxycarbonyl group, an ethoxycarbonyl group, an n-propoxycarbonyl group, an i-propoxycarbonyl group, an n-butoxycarbonyl group, and a t-butoxycarbonyl group;

C1 to C6 alkoxycarbonyloxy groups such as a methoxycarbonyloxy group, an ethoxycarbonyloxy group, an n-propoxycarbonyloxy group, an i-propoxycarbonyloxy group, an n-butoxycarbonyloxy group, and a t-butoxycarbonyloxy group;

a carboxyl group;

halogeno groups such as a fluoro group, a chloro group, a bromo group, and an iodo group;

C1 to C6 haloalkyl groups such as a chloromethyl group, a chloroethyl group, a trifluoromethyl group, a 1,2-dichloro-n-propyl group, a 2,2,2-trifluoroethyl group, and a 1-fluoro-n-butyl group;

C2 to C6 haloalkenyl groups such as a 2-chloro-1-propenyl group, and a 2-fluoro-1-butenyl group;

C2 to C6 haloalkynyl groups such as a 4,4-dichloro-1-butynyl group, a 4-fluoro-1-pentynyl group, and a 5-bromo-2-pentynyl group;

C1 to C6 haloalkoxy groups such as a trifluoromethoxy group, a 2,2,2-trifluoroethoxy group, and a 2,3-dichlorobutoxy group;

C2 to C6 haloalkenyloxy groups such as a 2-chloropropenyloxy group and a 3-bromobutenyloxy group;

C1 to C6 haloalkylcarbonyl groups such as a chloroacetyl group, a trifluoroacetyl group, and a trichloroacetyl group;

an amino group;

C1 to C6 alkyl-substituted amino groups such as a methylamino group, a dimethylamino group, and a diethylamino group;

an anilino group, a naphthylamino group;

phenyl C1 to C6 alkylamino groups such as a benzylamino group, and a phenethylamino group;

a formylamino group;

C1 to C6 alkylcarbonylamino groups such as an acetylamino group, a propanoylamino group, a butyrylamino group, and an i-propylcarbonylamino group;

C1 to C6 alkoxycarbonylamino groups such as a methoxycarbonylamino group, an ethoxycarbonylamino group, an n-propoxycarbonylamino group, and an i-propoxycarbonylamino group;

substituted or unsubstituted aminocarbonyl groups such as an aminocarbonyl group, a dimethylaminocarbonyl group, a phenylaminocarbonyl group, and an N-phenyl-N-methylaminocarbonyl group, imino C1 to C6 alkyl groups such as an iminomethyl group, a (1-imino)ethyl group, and a (1-imino)-n-propyl group;

substituted or unsubstituted imino C1 to C6 alkyl groups such as an N-hydroxy-iminomethyl group, a (1-(N-hydroxy)-imino) ethyl group, a (1-(N-hydroxy)-imino) propyl group, an N-methoxy-iminomethyl group, and a 1-(N-methoxy)-imino) ethyl group;

an aminocarbonyl group;

C1 to C6 alkyl-substituted aminocarbonyloxy groups such as an ethylaminocarbonyloxy group, and a dimethylaminocarbonyloxy group;

a mercapto group;

C1 to C6 alkylthio groups such as a methylthio group, an ethylthio group, an n-propylthio group, an i-propylthio group, an n-butylthio group, an i-butylthio group, an s-butylthio group, and a t-butylthio group;

C1 to C6 haloalkylthio groups such as a trifluoromethylthio group, and a 2,2,2-trifluoroethylthio group;

a phenylthio group;

5- to 6-membered heteroarylthio groups such as a thiazolylthio group, and a pyridylthio group;

C1 to C6 alkylsulfinyl groups such as a methylsulfinyl group, an ethylsulfinyl group, and a t-butylsulfinyl group;

C1 to C6 haloalkylsulfinyl groups such as a trifluoromethylsulfinyl group and a 2,2,2-trifluoroethylsulfinyl group;

a phenylsulfinyl group;

5- to 6-membered heteroarylsulfinyl groups such as a thiazolylsulfinyl group, and a pyridylsulfinyl group;

C1 to C6 alkylsulfonyl groups such as a methylsulfonyl group, an ethylsulfonyl group, and a t-butylsulfonyl group;

C1 to C6 haloalkylsulfonyl groups such as a trifluoromethylsulfonyl group and a 2,2,2-trifluoroethylsulfonyl group;

a phenylsulfonyl group;

5- to 6-membered heteroarylsulfonyl groups such as a thiazolylsulfonyl group, and a pyridylsulfonyl group;

C1 to C6 alkylsulfonyloxy groups such as a methylsulfonyloxy group, an ethylsulfonyloxy group, and a t-butylsulfonyloxy group;

C1 to C6 haloalkylsulfonyloxy groups such as a trifluoromethylsulfonyloxy group and a 2,2,2-trifluoroethylsulfonyloxy group;

tri (C1 to C6 alkyl)-substituted silyl groups such as a trimethylsilyl group, a triethylsilyl group, and a t-butyldimethylsilyl group;

a triphenylsilyl group;

a pentafluorosulfanyl group;

a cyano group; and a nitro group.

In addition, in these "substituents", any of the hydrogen atoms in any of the above substituents may be substituted with a group of a different structure. Examples of the "substituents" in such cases include C1 to C6 alkyl groups, C1 to C6 haloalkyl groups, C1 to C6 alkoxy groups, C1 to C6 haloalkoxy groups, halogeno groups, a cyano group and a nitro group.

In addition, the "3- to 6-membered heterocyclyl group" mentioned above is a 3-membered ring, 4-membered ring, 5-membered ring, or 6-membered ring group containing 1 to 4 heteroatoms selected from the group consisting of a nitrogen atom, an oxygen atom and a sulfur atom as a constitutional atom of the ring. The heterocyclyl group may be a monocyclyl group or a polycyclyl group. As long as at least one ring is a hetero ring in the polyheterocyclyl group, the remaining ring may be a saturated alicyclic ring, an unsaturated alicyclic ring or an aromatic ring. As examples of the "3- to 6-membered heterocyclyl group", mention may be made of a 3- to 6-membered saturated heterocyclyl group, a 5- to 6-membered heteroaryl group, a 5- to 6-membered unsaturated heterocyclyl group, and the like.

As examples of the 3- to 6-membered saturated heterocyclyl group, mention may be made of an aziridinyl group, an epoxy group, an azetidinyl group, a pyrrolidinyl group, a tetrahydrofuranyl group, a dioxolanyl group, a tetrahydropyranyl group, a piperidinyl group, a piperazinyl group, a morpholinyl group, a dioxanyl group, and the like.

As examples of the 5- to 6-membered unsaturated heterocyclyl group, mention may be made of a pyrrolinyl group, a dihydrofuranyl group, an imidazolinyl group, a pyrazolinyl group, an oxazolinyl group, an isooxazolinyl group, a thiazolinyl group, an isothiazolinyl group, a dihydropyranyl group, a dihydrooxadinyl group, and the like.

As examples of the "5-membered heteroaryl group", mention may be made of a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, a tetrazolyl group, and the like.

As examples of the "6-membered heteroaryl group", mention may be made of a pyridyl group, a pyrazinyl group, a pyrimidinyl group, a pyridazinyl group, a triazinyl group and the like.

[$R^1$]

$R^1$ represents a substituted or unsubstituted C1 to C6 alkyl group, a substituted or unsubstituted C2 to C6 alkenyl group, a substituted or unsubstituted C2 to C6 alkynyl group, or a substituted or unsubstituted C3 to C6 cycloalkyl group.

The "C1 to C6 alkyl group" for $R^1$ may be linear or branched. Examples of the "C1 to C6 alkyl group" include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, and an i-hexyl group.

Examples of the "C2 to C6 alkenyl group" for $R^1$ include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group and a 5-hexenyl group.

Examples of the "C2 to C6 alkynyl group" for $R^1$ include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group.

Examples of preferred substituents on the "C1 to C6 alkyl group", "C2 to C6 alkenyl group", and "C2 to C6 alkynyl group" for $R^1$ include halogeno groups such as a fluoro group, a chloro group, a bromo group, and an iodo group; a hydroxyl group; C1 to C6 alkoxy groups such as a methoxy group, an ethoxy group, an n-propoxy group, an i-propoxy group, an n-butoxy group, an s-butoxy group, an i-butoxy group, and a t-butoxy group; C1 to C6 haloalkoxy groups such as a 2-chloro-n-propoxy group, a 2,3-dichlorobutoxy group, and a trifluoromethoxy group; a phenyl group, a naphthyl group; a halogeno-substituted, C1 to C6 haloalkyl-substituted, or C1 to C6 haloalkoxy-substituted phenyl group such as a 4-chlorophenyl group, a 4-trifluoromethylphenyl group, a 4-trifluoromethoxyphenyl group; a halogeno-substituted, C1 to C6 haloalkyl-substituted, or C1 to C6 haloalkoxy-substituted naphthyl group; and a cyano group.

Examples of the "C3 to C6 cycloalkyl group" for $R^1$ include a cyclopropyl group, a cyclobutyl group, a cyclopentyl group, and a cyclohexyl group.

Examples of preferred substituents on the "C3 to C8 cycloalkyl group" for $R^1$ include halogeno groups such as a fluoro group, a chloro group, a bromo group, and an iodo group; a C1 to C6 alkyl group such as a methyl group, an ethyl group, an n-propyl group, an i-propyl group, an n-butyl group, an s-butyl group, an i-butyl group, a t-butyl group, an n-pentyl group, and an n-hexyl group; C1 to C6 haloalkyl groups such as a chloromethyl group, a chloroethyl group, a trifluoromethyl group, a 1,2-dichloro-n-propyl group, and a 1-fluoro-n-butyl group; a hydroxyl group; a C1 to C6 alkoxy group such as a methoxy group, an ethoxy group, an n-propoxy group, an i-propoxy group, an n-butoxy group, an s-butoxy group, an i-butoxy group, and a t-butoxy group; a C1 to C6 haloalkoxy group such as a 2-chloro-n-propoxy group, a 2,3-dichlorobutoxy group, and a trifluoromethoxy group; and a cyano group.

In the present invention, $R^1$ is preferably a substituted or unsubstituted C1 to C6 alkyl group, a substituted or unsubstituted C2 to C6 alkenyl group, or a substituted or unsubstituted C3 to C6 cycloalkyl group.

The substituent on the C1 to C6 alkyl group is preferably a halogeno group or a C1 to C6 alkoxy group.

[$R^2$]

$R^2$ represents a hydrogen atom, a substituted or unsubstituted C1 to C6 alkyl group, a substituted or unsubstituted C2 to C6 alkenyl group, a substituted or unsubstituted C2 to C6 alkynyl group, a group represented by $R^a$—CO—, a group represented by $R^aO$—CO—, a group represented by $R^aNH$—CO—, a group represented by $R^a_2N$—CO—, a group represented by $R^a$—$SO_2$—, a group represented by $R^a$—CO—O—$CR^b_2$—, or a group represented by $R^aO$—CO—O—$CR^b_2$—.

As examples of the a substituted or unsubstituted C1 to C6 alkyl group, the substituted or unsubstituted C2 to C6 alkenyl group, and the substituted or unsubstituted C2 to C6 alkynyl group for $R^2$, the same ones as listed for $R^1$ may be mentioned.

Each $R^a$ for the "group represented by $R^a$—CO—", the "group represented by $R^aNH$—CO—", the "group represented by $R^a_2N$—CO—", the "group represented by $R^a$—$SO_2$—", the "group represented by $R^a$—CO—O—$CR^b_2$—", and the "group represented by $R^aO$—CO—O—$CR^b_2$—" for $R^2$, independently represents a substituted or unsubstituted C1 to C6 alkyl group, a substituted or unsubstituted C2 to C6 alkenyl group, a substituted or unsubstituted C2 to C6 alkynyl group, a substituted or unsubstituted C3 to C6 cycloalkyl group, a substituted or unsubstituted phenyl group, a substituted or unsubstituted naphthyl group, or a substituted or unsubstituted 5- to 6-membered heterocyclyl group.

Examples of the "C1 to C6 alkyl group" for $R^a$ include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, an i-hexyl group, and the like.

Examples of the "C2 to C6 alkenyl group" for $R^a$ include a vinyl group, a 1-propenyl group, and the like.

Examples of the "C2 to C6 alkynyl group" for $R^a$ include an ethynyl group, a 1-propynyl group, and the like.

Examples of preferred substituents on the "C1 to C6 alkyl group", "C2 to C6 alkenyl group", and "C2 to C6 alkynyl group" for $R^a$ include halogeno groups such as a fluoro group, a chloro group, a bromo group, and an iodo group; a hydroxyl group; C1 to C6 alkoxy groups such as a methoxy group, an ethoxy group, an n-propoxy group, an i-propoxy group, an n-butoxy group, an s-butoxy group, an i-butoxy group, and a t-butoxy group; C1 to C6 haloalkoxy groups such as a 2-chloro-n-propoxy group, a 2,3-dichlorobutoxy group, and a trifluoromethoxy group; C3 to C6 cycloalkyl groups such as a cyclopropyl group, a cyclobutyl group, a cyclopentyl group, and a cyclohexyl group; a phenyl group, a naphthyl group; a halogeno-substituted, C1 to C6 haloalkyl-substituted, or C1 to C6 haloalkoxy-substituted phenyl group such as a 4-chlorophenyl group, a 4-trifluoromethylphenyl group, a 4-trifluoromethoxyphenyl group; a halogeno-substituted, C1 to C6 haloalkyl-substituted, or C1 to C6 haloalkoxy-substituted naphthyl group; and a cyano group.

Examples of the "C3 to C6 cycloalkyl group" for $R^a$ include a cyclopropyl group, a cyclobutyl group, a cyclopentyl group, a cyclohexyl group, and the like.

The "5- to 6-membered heterocyclyl group" for $R^a$ is a 5-membered ring or 6-membered ring group containing 1, 2, 3, or 4 heteroatoms selected from the group consisting of a nitrogen atom, an oxygen atom and a sulfur atom as a constitutional atom of the ring. In the case where there are 2 or more heteroatoms, they are the same or different. Examples of the "5- to 6-membered heterocyclyl group" include a 5- to 6-membered saturated heterocyclyl group, a 5- to 6-membered heteroaryl group, a 5- to 6-membered unsaturated heterocyclyl group, and the like.

Examples of the 5- to 6-membered saturated heterocyclyl group include a pyrrolidinyl group, a tetrahydrofuranyl group, a dioxolanyl group, a tetrahydropyranyl group, a piperidinyl group, a piperazinyl group, a morpholinyl group, a dioxanyl group, and the like.

Examples of the 5-membered unsaturated heterocyclyl group include a pyrrolinyl group, a dihydrofuranyl group, an imidazolinyl group, a pyrazolinyl group, an oxazolinyl group, an isoxazolinyl group, a thiazolidinyl group, an isothiazolidinyl group, and the like.

Examples of the 6-membered unsaturated heterocyclyl group include a dihydropyranyl group, a dihydrooxadinyl group, and the like.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, a tetrazolyl group, and the like.

Examples of the 6-membered heteroaryl group include a pyridyl group, a pyrazinyl group, a pyrimidinyl group, a pyridazinyl group, a triazinyl group and the like.

Examples of preferred substituents on the "C3 to C6 cycloalkyl group", "phenyl group", "naphthyl group" or "5- to 6-membered heterocyclyl group" for $R^a$ include halogeno groups such as a fluoro group, a chloro group, a bromo group, and an iodo group; C1 to C6 alkyl groups such as a methyl group, an ethyl group, an n-propyl group, an i-propyl group, an n-butyl group, an s-butyl group, an i-butyl group, a t-butyl group, an n-pentyl group, and an n-hexyl group; C1 to C6 haloalkyl groups such as a chloromethyl group, a chloroethyl group, a trifluoromethyl group, a 1,2-dichloro-n-propyl group, and a 1-fluoro-n-butyl group; a hydroxyl group; C1 to C6 alkoxy groups such as a methoxy group, an ethoxy group, an n-propoxy group, an i-propoxy group, an n-butoxy group, an s-butoxy group, an i-butoxy group, and a t-butoxy group; C1 to C6 haloalkoxy groups such as a 2-chloro-n-propoxy group, a 2,3-dichlorobutoxy group, and a trifluoromethoxy group; a phenyl group, a naphthyl group; a halogeno-substituted, C1 to C6 haloalkyl-substituted, or C1 to C6 haloalkoxy-substituted phenyl group such as a 4-chlorophenyl group, a 4-trifluoromethylphenyl group, or a 4-trifluoromethoxyphenyl group; a halogeno-substituted, C1 to C6 haloalkyl-substituted, or C1 to C6 haloalkoxy-substituted naphthyl group; and a cyano group.

Examples of the "group represented by $R^a$—CO—" for $R^2$ include an acetyl group, and the like.

Examples of the "group represented by $R^aO$—CO—" for $R^2$ include a methoxycarbonyl group, an ethoxycarbonyl group, and the like.

Examples of the "group represented by $R^aNH$—CO—" for $R^2$ include an N-methylaminocarbonyl group, an N-(i-propyl)aminocarbonyl group, and the like.

Examples of the "group represented by $R^a{}_2N$—CO—" for $R^2$ include an N,N-dimethylaminocarbonyl group, an N-(i-propyl)-N-methylaminocarbonyl group, and the like.

Examples of the "group represented by $R^a$—$SO_2$—" for $R^2$ include a methanesulfonyl group and the like.

In the "group represented by $R^a$—CO—O—$CR^b{}_2$—" or the "group represented by $R^aO$—CO—O—$CR^b{}_2$—" for $R^2$, each $R^b$ independently represents a hydrogen atom or a substituted or unsubstituted C1 to C6 alkyl group.

As examples of the "C1 to C6 alkyl group" for $R^b$, the same ones as listed for $R^a$ may be mentioned. In addition, as examples of the substituents on the "C1 to C6 alkyl group" for $R^b$, the same ones as listed for $R^a$ may be mentioned.

Examples of the "group represented by $R^a$—CO—O—$CR^b{}_2$—" for $R^2$ include an acetoxymethyl group, an isopropylcarbonyloxymethyl group, a 1-acetoxyethyl group, a 1-isopropylcarbonyloxyethyl group, and the like.

Examples of the "group represented by $R^a$ O—CO—O—$CR^b{}_2$—" for $R^2$ include a methoxycarbonyloxymethyl group, an isopropyloxycarbonyloxymethyl group, a 1-(methyloxycarbonyloxy)ethyl group, a 1-(isopropyloxycarbonyloxy)ethyl group, and the like.

In the present invention, $R^2$ is preferably a hydrogen atom, a substituted or unsubstituted C1 to C6 alkyl group, a group represented by $R^a$—CO—, a group represented by $R^aO$—CO—, a group represented by $R^a$—$SO_2$—, a group represented by $R^a$—CO—O—$CR^b{}_2$—, or a group represented by $R^aO$—CO—O—$CR^b{}_2$—.

$R^a$ is preferably a substituted or unsubstituted C1 to C6 alkyl group, a substituted or unsubstituted phenyl group, or a substituted or unsubstituted 5- to 6-membered heterocyclyl group.

$R^b$ is preferably a hydrogen atom, or a substituted or unsubstituted C1 to C6 alkyl group.

Examples of preferable substituents on the "C1 to C6 alkyl group" for $R^2$ include a halogeno group, a C1 to C6 alkoxy group, a C1 to C6 haloalkoxy group, a phenyl group; a halogeno-substituted, C1 to C6 haloalkyl-substituted, or C1 to C6 haloalkoxy-substituted phenyl group; or a cyano group. In particular, a C1 to C6 alkoxy group, a phenyl group; or a halogeno-substituted, C1 to C6 haloalkyl-substituted, or C1 to C6 haloalkoxy-substituted phenyl group is preferable.

[$R^3$]

$R^3$ represents a hydrogen atom, a substituted or unsubstituted C1 to C6 alkyl group, a substituted or unsubstituted C2 to C6 alkenyl group, a substituted or unsubstituted C2 to C6 alkynyl group, or a substituted or unsubstituted C3 to C6 cycloalkyl group.

As examples of the substituted or unsubstituted C1 to C6 alkyl group, the substituted or unsubstituted C2 to C6 alkenyl group, the substituted or unsubstituted C2 to C6 alkynyl group, or the substituted or unsubstituted C3 to C6 cycloalkyl group for $R^3$, the same ones listed for $R^1$ may be mentioned.

In the present invention, $R^3$ is preferably a hydrogen atom, a substituted or unsubstituted C1 to C6 alkyl group, or a substituted or unsubstituted C3 to C6 cycloalkyl group.

The substituent on the C1 to C6 alkyl group is preferably a halogeno group.

The substituent on the C3 to C6 cycloalkyl group is preferably a halogeno group or a C1 to C6 alkyl group.

[$R^4$]

$R^4$ represents a halogeno group, a substituted or unsubstituted C1 to C6 alkyl group, a substituted or unsubstituted C1 to C6 alkoxy group, a substituted or unsubstituted phenyl group, a substituted or unsubstituted naphthyl group, a substituted or unsubstituted 5- to 6-membered heteroaryl group, or a cyano group.

Examples of the "halogeno group" for $R^4$ include a fluoro group, a chloro group, a bromo group, an iodo group, and the like.

The "C1 to C6 alkyl group" for $R^4$ may be linear or branched. Examples of the "C1 to C6 alkyl group" for $R^4$ include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, an i-hexyl group, and the like.

Examples of the "C1 to C6 alkoxy group" for $R^4$ include a methoxy group, an ethoxy group, an n-propoxy group, an n-butoxy group, an n-pentyloxy group, an n-hexyloxy group, an i-propoxy group, an i-butoxy group, an s-butoxy group, a t-butoxy group, an i-hexyloxy group, and the like.

Examples of preferred substituents on the "C1 to C6 alkyl group" or the "C1 to C6 alkoxy group" for $R^4$ include halogeno groups such as a fluoro group, a chloro group, a bromo group, and an iodo group; a hydroxyl group; C1 to C6 alkoxy groups such as a methoxy group, an ethoxy group, an n-propoxy group, an i-propoxy group, an n-butoxy group, an s-butoxy group, an i-butoxy group, and a t-butoxy group; C1 to C6 haloalkoxy groups such as a 2-chloro-n-propoxy group, a 2,3-dichlorobutoxy group, and a trifluoromethoxy group; a phenyl group, a naphthyl group; a halogeno-substituted, C1 to C6 haloalkyl-substituted, or C1 to C6 haloalkoxy-substituted phenyl group such as a 4-chlorophenyl group, a 4-trifluoromethylphenyl group, a 4-trifluoromethoxyphenyl group; a halogeno-substituted, C1 to C6 haloalkyl-substituted, or C1 to C6 haloalkoxy-substituted naphthyl group; and a cyano group.

The "5- to 6-membered heteroaryl group" for $R^4$ is a 5-membered aromatic ring, or 6-membered aromatic ring group containing 1, 2, 3, or 4 heteroatoms selected from the group consisting of a nitrogen atom, an oxygen atom and a sulfur atom as a constitutional atom of the ring. When there are two or more heteroatoms, they may be the same or different.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, a tetrazolyl group, and the like.

Examples of the 6-membered heteroaryl group include a pyridyl group, a pyrazinyl group, a pyrimidinyl group, a pyridazinyl group, a triazinyl group and the like.

Examples of preferred substituents on the "phenyl group", "naphthyl group" or "5- to 6-membered heteroaryl group" for $R^4$ include halogeno groups such as a fluoro group, a chloro group, a bromo group, and an iodo group; C1 to C6 alkyl groups such as a methyl group, an ethyl group, an n-propyl group, an i-propyl group, an n-butyl group, an s-butyl group, an i-butyl group, a t-butyl group, an n-pentyl group, and an n-hexyl group; C1 to C6 haloalkyl groups such as a chloromethyl group, a chloroethyl group, a trifluoromethyl group, a 1,2-dichloro-n-propyl group, and a 1-fluoro-n-butyl group; a hydroxyl group; C1 to C6 alkoxy groups such as a methoxy group, an ethoxy group, an n-propoxy group, an i-propoxy group, an n-butoxy group, an s-butoxy group, an i-butoxy group, and a t-butoxy group; C1 to C6 haloalkoxy groups such as a 2-chloro-n-propoxy group, a 2,3-dichlorobutoxy group, and a trifluoromethoxy group; and a cyano group.

In the present invention, $R^4$ is preferably a halogeno group, a substituted or unsubstituted C1 to C6 alkyl group, a substituted or unsubstituted C1 to C6 alkoxy group, or a cyano group.

The substituent on the C1 to C6 alkyl group or the C1 to C6 alkoxy group is preferably a halogeno group.

[$R^5$, $R^6$]

$R^5$ represents a hydrogen atom, or a halogeno group.

$R^6$ represents a hydrogen atom, or a halogeno group. $R^6$ is preferably a hydrogen atom.

[A]

A represents a substituted or unsubstituted C1 to C4 alkylene group, a substituted or unsubstituted C2 to C3 alkenylene group, or a substituted or unsubstituted C1 to C2 alkyleneoxy C1 to C2 alkylene group.

Examples of the "C1 to C4 alkylene group" include a methylene group, a dimethylene group, a trimethylene group, a tetramethylene group, and the like.

Examples of the "C2 to C3 alkenylene group" include a vinylene group (—CH═CH—), a propenylene group (—CH═CH—CH$_2$— or —CH$_2$—CH═CH—) and the like.

Examples of the "C1 to C2 alkyleneoxy C1 to C2 alkylene group" include a methyleneoxymethylene group (—CH$_2$—O—CH$_2$—), a methyleneoxydimethylene group (—CH$_2$—O—CH$_2$CH$_2$—), a dimethyleneoxymethylene group (—CH$_2$CH$_2$—O—CH$_2$—), a dimethyleneoxydimethylene group (—CH$_2$CH$_2$—O—CH$_2$CH$_2$—), and the like.

Examples of the substituents on the "C1 to C4 alkylene group", the "C2 to C3 alkenylene group", or the "C1 to C2 alkyleneoxy C1 to C2 alkylene group" include halogeno groups such as a fluoro group, a chloro group, a bromo group, and an iodo group; C1 to C6 alkyl groups such as a methyl group, an ethyl group, an n-propyl group, an i-propyl group, an n-butyl group, an s-butyl group, an i-butyl group, and a t-butyl group; C1 to C6 haloalkyl groups such as a chloromethyl group, a chloroethyl group, a trifluoromethyl group, a 1,2-dichloro-n-propyl group, and a 1-fluoro-n-butyl group; a hydroxyl group; C1 to C6 alkoxy groups such as a methoxy group, an ethoxy group, an n-propoxy group, an i-propoxy group, an n-butoxy group, an s-butoxy group, an i-butoxy group, and a t-butoxy group; C1 to C6 haloalkoxy groups such as a 2-chloro-n-propoxy group, a 2,3-dichlorobutoxy group, and a trifluoromethoxy group; C1 to C6 alkoxy C1 to C6 alkyl groups such as a methoxymethyl group; a phenyl group, a nathphyl group; halogeno-substituted, C1 to C6 haloalkyl-substituted, or C1 to C6 haloalkoxy-substituted phenyl groups such as a 4-chlorophenyl group, a 4-trifluoromethylphenyl group, and 4-trifluoromethoxyphenyl group; halogeno-substituted, C1 to C6 haloalkyl-substituted, or C1 to C6 haloalkoxy-substituted nathphyl groups; and a cyano group.

In the present invention, A is preferably a substituted or unsubstituted C1 to C4 alkylene group.

Preferable examples of the substituent on the C1 to C4 alkylene group include a C1 to C6 alkyl group, or a halogeno group.

[$X^1$, $X^2$, $R^c$, m, and n]

$X^1$ represents an oxygen atom, or a sulfonyl group.

$X^2$ represents an oxygen atom, a sulfenyl group, a sulfinyl group, a sulfonyl group, a group represented by —S(═NR$^c$)—, or a group represented by —S(═O)(═NR$^c$)—.

Each $R^c$ independently represents a hydrogen atom, a substituted or unsubstituted C1 to C6 alkyl group, a substituted or unsubstituted phenyl group, a substituted or unsubstituted naphthyl group, or a cyano group. As examples of the "C1 to C6 alkyl group" for $R^c$, mention may be made of the same ones listed in R.

m represents 0 or 1, and n represents 0 or 1. The sum of m and n is 1 or 2. When A is a substituted or unsubstituted methylene group, the sum of m and n is 2.

In the present invention, $X^1$ is preferably an oxygen atom or a sulfonyl group, and $X^2$ is preferably an oxygen atom, a sulfenyl group, or a sulfonyl group.

In the present invention, a compound represented by formula (I-2) is preferable in which A is a trimethylene group, m is 0, and n is 1.

[Chem. 3]

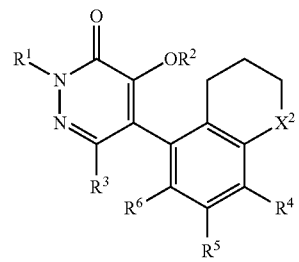

(I-2)

In formula (I-2), $X^2$, and $R^1$ to $R^6$ represent the same meanings as those defined in formula (I).

In the present invention, a compound represented by formula (I-1) is preferable in which A is a trimethylene group, $R^5$ and $R^6$ represent a hydrogen atom, m is 0, and n is 1.

[Chem. 4]

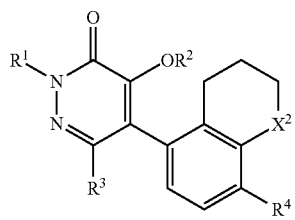

(I-1)

In formula (I-1), $X^2$, and $R^1$ to $R^4$ represent the same meanings as those defined in formula (I).

[Salt]

Examples of salts of compound (I) include a salt of an alkali metal such as lithium, sodium, or potassium; a salt of an alkaline earth metal such as calcium or magnesium; a salt of a transition metal such as iron or copper; an ammonium salt; a salt of an organic base such as triethylamine, tributylamine, pyridine, or hydrazine; and the like.

The structure of the compound (I) or the salt of compound (I) can be identified by NMR spectra, IR spectra, MS spectra or the like.

Compound (I) is not particularly limited by a method for preparing the same. In addition, the salt of compound (I) can be obtained by a known method from compound (I). Compound (I) can be produced by a method described in Examples and the like by for example, using a compound obtained by the method described in Patent Document 1 as an intermediate for preparation.

(Reaction Scheme 1)

For example, a compound wherein $R^2$ is other than a lower alkyl group or a hydrogen atom (compound of formula (I-a)) among compounds (I) can be prepared from compound of formula (I-b), as shown in the following reaction scheme 1. Formula (I-b) represents a compound wherein $R^2$ is a hydrogen atom in compounds (I). The symbols shown in formula (I-a) and formula (I-b) represent the same meanings as those defined in formula (I). Xa in formula (2) represents a halogeno group such as a chloro group, or a bromo group. $R^{2a}$ in formula (2) represents $R^2$ other than a lower alkyl group or a hydrogen atom.

[Chem. 6]

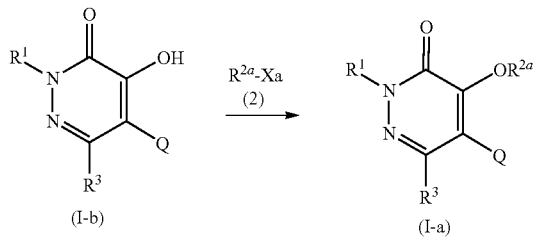

The compound of formula (I-a) can be prepared by reacting the compound of formula (I-b) with the compound of formula (2) in the presence of a suitable base (for example, an inorganic base such as potassium carbonate).

(Reaction Scheme 2)

The compound of formula (I-b) can be prepared from a compound of formula (I-c) as shown in the following reaction scheme 2. The symbols shown in formula (I-c) and formula (I-b) represent the same meanings as those defined in formula (I). $R^{2a}$ represents a lower alkyl group such as a methyl group. Hereinafter, $R^{2a}$ represents the same meaning.

[Chem. 6]

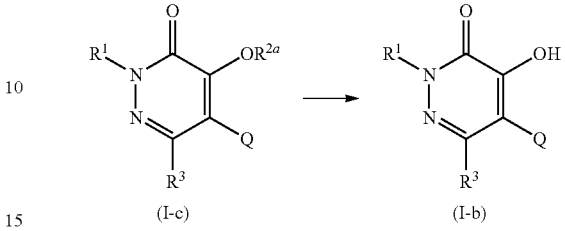

The compound of formula (I-b) can be prepared by heating the compound of formula (I-c) together with morpholine.

(Reaction Scheme 3)

The compound of formula (I-c) can be prepared by subjecting a compound of formula (4) and a compound of formula (5) to condensation, as shown in the following reaction scheme 3.

The symbols shown in formula (4) represent the same meanings as those defined in formula (I). $R^y$ represents a lower alkyl group such as a methyl group or an ethyl group. In addition, $R^y$ may be bonded to another $R^y$ to form a 1,3,2-dioxaborolane ring. Q in formula (5) means a moiety of benzene ring having a substituent $R^4$ in formula (I). $X^b$ represents a halogeno group.

[Chem. 7]

The compound of formula (I-c) can be prepared by reacting a compound of formula (4) with a compound of formula (5) in the presence of a suitable base (for example, an inorganic base such as potassium phosphate or cesium fluoride), a metal catalyst (for example, a palladium catalyst such as $Pd(OAc)_2$), and optionally a ligand (for example, a phosphine ligand).

The metal catalyst and the ligand can be added as a pre-formed complex (for example, a palladium/phosphine complex such as bis(triphenylphosphine) palladium or [1,1-bis(diphenylphosphino)ferrocene] palladium dichloride dichloromethane adduct).

(Reaction Scheme 4)

The compound of formula (4) can be prepared from a compound of formula (6), as shown in the following reaction scheme 4. The symbols shown in formula (6) represent the same meanings as those defined in formula (I).

[Chem. 8]

(6) → (4)

The compound of formula (4) can be prepared by reacting a compound of formula (6) with boronic acid or an ester of boronic acid such as bis(pinacolato)diboron in the presence of a suitable base (for example, an inorganic base such as potassium phosphate or cesium fluoride), a metal catalyst (for example a palladium catalyst such as $Pd_2(dba)_3$, or $Pd(OAc)_2$ and optionally a ligand (for example, a phosphine ligand).

The metal catalyst and the ligand can be added as a pre-formed complex (for example, a palladium/phosphine complex such as bis(triphenylphosphine) palladium dichloride or [1,1-bis(diphenylphosphino)ferrocene] palladium dichloride dichloromethane adduct).

(Reaction Scheme 5)

The compound of formula (6) can be prepared from a compound of formula (7), as shown in the following reaction scheme 5.

[Chem. 9]

(7) → (6)

The compound of formula (6) can be prepared by reacting the compound of formula (7) with a suitable metal alkoxide such as sodium methoxide.

The compound of formula (7) can be prepared by a known method.

(Reaction Scheme 3A)

The compound of formula (I-c) can be prepared by subjecting the compound of formula (6) and a compound of formula (8) to condensation, as shown in the following reaction scheme 3A.

Q in formula (8) means a benzene ring moiety having a substituent $R^4$ in formula (I). $X^b$ represents a halogeno group. $R^y$ represents a lower alkyl group such as a methyl group or an ethyl group. In addition, $R^y$ may be bonded to another $R^y$ to form a 1,3,2-dioxaborolane ring.

[Chem. 10]

(6) + (8) → (I-c)

The compound of formula (I-c) can be prepared by reacting the compound of formula (6) with the compound of formula (8) in the presence of a suitable base (for example, an inorganic base such as potassium phosphate or cesium fluoride), a metal catalyst (for example, a palladium catalyst such as $Pd(OAc)_2$), and optionally a ligand (for example a phosphine ligand).

The metal catalyst and the ligand can be added as a pre-formed complex (for example, a palladium/phosphine complex such as bis(triphenylphosphine) palladium dichloride or [1,1-bis(diphenylphosphino)ferrocene] palladium dichloride dichloromethane adduct).

The compound of the present invention exhibits high herbicidal activity in both methods of soil treatment and foliage (shoot) treatment under upland farming conditions.

The compound of the present invention is effective against various field weeds and may show selectivity to crops such as maize and wheat.

The herbicide of the present invention contains at least one selected from the group consisting of the compound (I) and a salt of the compound (I) as an active ingredient.

That is, one aspect of the present invention is a herbicide containing at least one selected from the group consisting of the compound (I) and a salt thereof as an active ingredient.

The herbicide of the present invention exhibits high herbicidal activity in both methods of soil treatment and foliage treatment under upland farming conditions.

In addition, the herbicide of the present invention has excellent herbicidal effects on paddy weeds such as *Echinochloa* spp., *Cyperus difforis*, *Sagittaria trifolia* and *Schoenoplectiella hotarui*, and may show selectivity to rice.

Furthermore, the herbicide of the present invention can also be applied for the control of weeds in places such as orchards, lawns, track ends and vacant sites.

Useful plants for which the herbicide of the present invention can be used include crops such as barley and wheat, cotton, rapeseed, sunflower, maize, rice, soybean, sugar beet, sugar cane and lawn.

Crops may also include trees such as fruit trees, palm trees, coconut trees or other nuts, and also include vines such as grapes, fruit shrubs, fruit plants and vegetables.

Examples of upland field weeds to be controlled include the following weeds.

(A) Monocotyledonous Weeds (1) Weeds of the Family Cyperaceae

Weeds of the genus *Cyperus* such as *Cyperus esculentus, Cyperus iria, Cyperus microiria* and *Cyperus rotundus*.

(2) Weeds of the Family Poaceae

Weeds of the genus *Alopecurus* such as *Alopecurus aequalis* and *Alopecurus myosuroides;*

Weeds of the genus *Apera* such as *Apera spica-venti;*

Weeds of the genus *Avena* such as *Avena sativa;*

Weeds of the genus *Bromus* such as *Bromus japonicus* and *Bromus sterilis;*

Weeds of the genus *Digitaria* such as *Digitaria ciliaris* and *Digitaria sanguinalis*;

Weeds of the genus *Echinochloa* such as *Echinochloa crus-galli*;

Weeds of the genus *Eleusine* such as *Eleusine indica*;

Weeds of the genus *Lolium* such as *Lolium multiflorum* Lam.;

Weeds of the genus *Panicum* such as *Panicum dichotomiflorum*;

Weeds of the genus *Poa* such as *Poa annua*;

Weeds of the genus *Setaria* such as *Setaria faberi*, *Setaria pumila* and *Setaria viridis*;

Weeds of the genus *Sorghum* such as *Sorghum bicolor*; and

Weeds of the genus *Urochloa* such as *Urochloa platyphylla*.

(B) Dicotyledonous Weeds (1) Weeds of the Family Amaranthaceae

Weeds of the genus *Amaranthus* such as *Amaranthus blitum*, *Amaranthus palmeri*, *Amaranthus retroflexus* and *Amaranthus rudis*;

Weeds of the genus *Chenopodium* such as *Chenopodium album*;

Weeds of the genus *Bassia* such as *Bassia scoparia*.

(2) Weeds of the Family Asteraceae

Weeds of the genus *Ambrosia* such as *Ambrosia artemisiifolia* and *Ambrosia trifida*;

Weeds of the genus *Conyza* such as *Conyza canadensis* and *Conyza sumatrensis*;

Weeds of the genus Erigeron such as Erigeron *annuus*;

Weeds of the genus *Matricaria* such as *Matricaria inodora* and *Matricaria recutita*;

Weeds of the genus *Xanthium* such as *Xanthium occidentale*.

(3) Weeds of the Family Caryophyllaceae

Weeds of the genus *Sagina* such as *Sagina japonica*;

Weeds of the genus *Stellaria* such as *Stellaria media*.

(4) Weeds of the Family Convolvulaceae

Weeds of the genus *Calystegia* such as *Calystegia japonica*;

Weeds of the genus *Ipomoea* such as *Ipomoea coccinea*, *Ipomoea hederacea*, *Ipomoea lacunosa* and *Ipomoea triloba*.

(5) Weeds of the Family Lamiaceae

Weeds of the genus *Lamium* such as *Lamium album* var. *barbatum*, *Lamium amplexicaule* and *Lamium purpureum*.

(6) Weeds of the Family Malvaceae

Weeds of the genus *Abutilon* such as *Abutilon theophrasti*;

Weeds of the genus *Sida* such as *Sida spinosa*.

(7) Weeds of the Family Plantaginaceae

Weeds of the genus *Veronica* such as *Veronica persica*.

(8) Weeds of the Family Polygonaceae

Weeds of the genus *Fallopia* such as *Fallopia convolvulus*.

Weeds of the genus *Persicaria* such as *Persicaria lapathifolia* and *Persicaria longiseta*.

(9) Weeds of the Family Rubiaceae

Weeds of the genus *Galium*, such as *Galium spurium* var. *echinospermon*.

Examples of paddy weeds to be controlled include the following weeds.

(A) Monocotyledonous Weeds (1) Weeds of the Family Alismataceae

Weeds of the genus *Sagittaria* such as *Sagittaria pygmaea* Miq. and *Sagittaria trifolia*.

(2) Weeds of the Family Cyperaceae

Weeds of the genus *Cyperus* such as *Cyperus serotinus* and *Cyperus difforis*;

Weeds of the genus *Eleocharis* such as *Eleocharis kuroguwai* Ohwi;

Weeds of the genus *Schoenoplectiella* such as *Schoenoplectiella hotarui* and Schoenoplectiellajuncoides Roxb.

Weeds of the genus *Scirpus* such as *Scirpus maritimus* (*Scirpus* martimus) and *Scirpus nipponicus*.

(3) Weeds of the Family Poaceae

Weeds of the genus *Echinochloa* such as *Echinochloa oryzoides* and *Echinochloa crus-galli*;

Weeds of the genus *Leersia* such as *Leersia japonica*;

Weeds of the genus *Paspalum* such as *Paspalum distichum*.

(4) Weeds of the Family Pontederiaceae

Weeds of the genus *Monochoria* such as *Monochoria korsakowii* and *Monochoria vaginalis* var. *plantaginea*.

(B) Dicotyledonous Weeds (1) Weeds of the Family Apiaceae

Weeds of the genus *Oenanthe* such as *Oenanthe javanica*.

(2) Weeds of the Family Elatinaceae

Weeds of the genus *Elatine* such as *Elatine triandra*.

(3) Weeds of the Family Lindemiaceae

Weeds of the genus *Lindernia* such as *Lindernia dubia* subsp. major, *Lindernia dubia* subsp. *dubia* and *Lindernia procumbens*.

(4) Weeds of the Family Lythraceae

Weeds of the genus *Rotala* such as *Rotala indica* var. *uliginosa*.

In addition, the present invention relates to a method for controlling weeds of monocotyledonous species and/or dicotyledonous species in useful plants, including the step of applying the compound (I) or a salt thereof, or a herbicide containing the compound (I), to the aforementioned weeds and/or the aforementioned plants and/or locuses thereof.

Use of the method of the present invention makes it possible to selectively control weeds even at locuses containing useful plants and/or weeds.

In addition, weeds can be controlled even at locuses where useful plants will grow, other than locuses where useful plants have grown. The application of the herbicide can be generally carried out by a method such as spraying, powder-scattering, drip-irrigating, irrigating, mixing, according to the dosage form of the herbicide.

The herbicide of the present invention may consist only of the compound of the present invention, or may be formulated into a dosage form generally adopted as an agricultural chemical, for example, a wettable powder, a granule, a powder, an emulsiable concentrate, a water soluble powder, a suspension, a flowable or the like.

A known additive or carrier can be used for formulation.

That is, one aspect of the present invention is a herbicide containing an agrochemically acceptable solid carrier and/or liquid carrier.

For solid dosage forms, vegetable powders such as soy flour and wheat flour, fine mineral powders such as diatomaceous earth, apatite, gypsum, talc, bentonite, pyrophyllite and clay, and solid carriers of organic and inorganic compounds such as sodium benzoate, urea and mirabilite can be used.

For liquid dosage forms, petroleum fractions such as kerosine, xylene and solvent naphtha, and liquid carriers such as cyclohexane, cyclohexanone, dimethylformamide, dimethyl sulfoxide, alcohol, acetone, trichloroethylene, methyl isobutyl ketone, mineral oil, vegetable oil and water can be used.

In the formulation, a surfactant can be added as needed. Examples of the surfactant include nonionic surfactants such as alkylphenyl ethers to which polyoxyethylene is added, alkyl ethers to which polyoxyethylene is added, higher fatty acid esters to which polyoxyethylene is added, sorbitan higher fatty acid esters to which polyoxyethylene is added, and tristyrylphenyl ethers to which polyoxyethylene is added, sulfuric acid ester salts of alkylphenyl ethers to which polyoxyethylene is added, alkylnaphthalene sulfonate, polycarboxylate, lignin sulfonate, formaldehyde condensates of alkylnaphthalene sulfonate, and isobutylene-maleic anhydride copolymers.

In the herbicide of the present invention, the concentration of the active ingredient can be appropriately set according to the dosage form. For example, the concentration of the active ingredient in a wettable powder preferably ranges from 5 to 90% by weight, and more preferably ranges from 10 to 85% by weight. The concentration of the active ingredient in an emulsifiable concentrate preferably ranges from 3 to 70% by weight, and more preferably ranges from 5 to 60% by weight. The concentration of the active ingredient in a granule preferably ranges from 0.01 to 50% by weight, and more preferably ranges from 0.05 to 40% by weight.

The wettable powder or emulsifiable concentrate obtained in this manner can be used as a suspension or emulsion by diluting with water to a predetermined concentration, and the granules can be directly sprayed on or mixed with the soil before or after germination of weeds. When the herbicide of the present invention is applied to a farm field, an appropriate amount of 0.1 g or more of the active ingredient per hectare can be applied.

In addition, the herbicide of the present invention can also be used by mixing with a known fungicide, fungicidal active ingredient, insecticide, insecticidal active ingredient, acaricide, acaricidal active ingredient, herbicide, herbicidal active ingredient, plant growth regulator, fertilizer, phytotoxicity reducer (safener) or the like. In particular, it is possible to reduce the amount of drug used by using it in combination with a herbicide. Further, in addition to labor saving, even better effects can also be expected due to the synergistic action of the mixed drug. In that case, a combination with a plurality of known herbicides is also possible.

That is, one aspect of the present invention is a herbicide containing one or more additional herbicidal active ingredients.

Further, one aspect of the present invention is a herbicide containing one or more additional safeners.

Other herbicidal active ingredients used in the present invention are not particularly limited, and examples thereof include the following.

(a) Aryloxyphenoxypropionic acid ester-based ingredients such as clodinafop-propargyl, cyhalofop-butyl, diclofop-methyl, fenoxaprop-P-ethyl, fluazifop-P, fluazifop-P-butyl, haloxyfop-methyl, pyriphenop-sodium, propaquizafop, quizalofop-P-ethyl and metamifop; cyclohexanedione-based ingredients such as alloxydim, butroxydim, clethodim, cycloxydim, profoxydim, sethoxydim, tepraloxydim and tralkoxydim; phenylpyrazolin-based ingredients such as pinoxaden; and other ingredients that are said to exhibit herbicidal efficacies by inhibiting acetyl CoA carboxylase of plants.

(b) Sulfonylurea-based ingredients such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron, foramsulfuron, halosulfuron-methyl, imazosulfuron, iodosulfuron-methyl, mesosulfuron, mesosulfuron-methyl, metsulfuron-methyl, nicosulfuron, oxasulfuron, primisulfuron, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron, orthosulfamuron, propyrisulfuron, flucetosulfuron, metazosulfuron, methiopyrsulfuron, monosulfuron-methyl, orthosulfuron and iofensulfuron; imidazolinone-based ingredients such as imazapic, imazamethabenz, imazamox-ammonium, imazapyr, imazaquin and imazethapyr; triazolopyrimidine sulfonamide-based ingredients such as cloransulam-methyl, diclosulam, florasulam, flumetsulam, metosulam, penoxsulam, pyroxsulam and metosulfam; pyrimidinyl(thio)benzoate-based ingredients such as bispyribac-sodium, pyribenzoxim, pyriftalid, pyrithiobac-sodium, pyriminobac-methyl and pyrimisulfan; sulfonyl amino carbonyl triazolinone-based ingredients such as flucarbazone, propoxycarbazone and thiencarbazone-methyl; sulfonanilide-based ingredients such as triafamone; and other ingredients that are said to exhibit herbicidal efficacies by inhibiting acetolactate synthase (ALS) (acetohydroxy acid synthase (AHAS)) of plants.

(c) Triazine-based ingredients such as ametryn, atrazine, cyanazine, desmetryne, dimethametryn, prometon, prometryn, propazine-based ingredients (propazine), CAT (simazine), simetryn, terbumeton, terbuthylazine, terbutryne, trietazine, atratone and cybutryne; triazinone-based ingredients such as hexazinone, metamitron and metribuzin; triazolinone-based ingredients such as amicarbazone; uracil-based ingredients such as bromacil, lenacil and terbacil; pyridazinone-based ingredients such as PAC (chloridazon); carbamate-based ingredients such as desmedipham, phenmedipham and swep; urea-based ingredients such as chlorobromuron, chlorotoluron, chloroxuron, dimefuron, DCMU (diuron), ethidimuron, fenuron, fluometuron, isoproturon, isouron, linuron, methabenzthiazuron, metobromuron, metoxuron, monolinuron, neburon, siduron, tebuthiuron, metobenzuron and karbutilate; amide-based ingredients such as DCPA (propanil) and CMMP (pentanochlor); anilide-based ingredients such as cypromid; nitrile-based ingredients such as bromofenoxim, bromoxynil and ioxynil; benzothiadiazinone-based ingredients such as bentazone; phenylpyridazine-based ingredients such as pyridate and pyridafol; and other ingredients that are said to exhibit herbicidal efficacies by inhibiting photosynthesis of plants such as methazole.

(d) Bipyridylium-based ingredients such as diquat and paraquat; and other ingredients that are said to become free radicals themselves in plants and generate active oxygen to exhibit fast-acting herbicidal effects.

(e) Diphenyl ether-based ingredients such as acifluorfen-sodium, bifenox, chlomethoxynil (chlomethoxyfen), fluoroglycofen, fomesafen, halosafen, lactofen, oxyfluorfen, nitrofen and ethoxyfen-ethyl; phenylpyrazole-based ingredients such as fluazolate and pyraflufen-ethyl; N-phenylphthalimide-based ingredients such as cinidon-ethyl, flumioxazin, flumiclorac-pentyl and chlorphthalim; thiadiazole-based ingredients such as fluthiacet-methyl and thidiazimin; oxaziazole-based ingredients such as oxadiazon and oxadiargyl; triazolinone-based ingredients such as azafenidin, carfentrazone-ethyl, sulfentrazone and bencarbazone; oxazolidinedione-based ingredients such as pentoxazone; pyrimidinedione-based ingredients such as benzfendizone and butafenacil; sulfonylamide-based ingredients such as saflufenacil; pyridazine-based ingredients such as flufenpyr-ethyl; and other ingredients that are said to exhibit herbicidal efficacies by inhibiting chlorophyll biosynthesis in plants and abnormally accumulating photosensitizing peroxide substances in plant bodies, such as pyrachlonil, profluazol, tiafenacil and trifludimoxazin.

(f) Pyridazinone-based ingredients such as norflurazon and metflurazon; pyridinecarboxamide-based ingredients such as diflufenican and picolinafen; triketone-based ingredients such as mesotrione, sulcotrione, tefuryltrione, tembotrione, bicyclopyrone and fenquinotrione; isoxazole-based ingredients such as isoxachlortole and isoxaflutole; pyrazole-based ingredients such as benzofenap, pyrazolynate, pyrazoxyfen, topramezone, pyrasulfotole and tolpyralate; triazole-based ingredients such as ATA (amitrol); isooxazolidinone-based ingredients such as clomazone; diphenyl ether-based ingredients such as aclonifen; and other ingredients that are said to exhibit herbicidal efficacies by inhibiting the biosynthesis of plant pigments such as carotenoids characterized by a bleaching action such as beflubutamid, fluridone, flurochloridone, flurtamone, benzobicyclone, methoxyphenone and ketospiradox.

(g) Glycine-based ingredients such as glyphosate, glyphosate-ammonium, glyphosate-isopropylamine and glyphosate trimesium (sulfosate); and other ingredients inhibiting EPSP synthase (h) Phosphinic acid-based ingredients inhibiting glutamine synthetase such as glufosinate, glufosinate-ammonium, and bialaphos (bilanafos), and other ingredients that are said to exhibit herbicidal efficacies by inhibiting the amino acid biosynthesis of plants.

(i) Carbamate-based ingredients such as asulam; and other ingredients inhibiting DHP (dihydropteroate) synthase (j) Dinitroaniline-based ingredients such as bethrodine (benfluralin), butralin, dinitramine, ethalfluralin, oryzalin, pendimethalin, trifluralin, nitralin and prodiamine; phosphoroamidate-based ingredients such as amiprofos-methyl and butamifos; pyridine-based ingredients such as dithiopyr and thiazopyr; benzamide-based ingredients such as propyzamide and tebutam; benzoic acid-based ingredients such as chlorthal and TCTP (chlorthal-dimethyl); carbamate-based ingredients such as IPC (chlorpropham), propham, carbetamide and barban; arylalanine-based ingredients such as flamprop-M and flamprop-M-isopropyl; chloroacetamide-based ingredients such as acetochlor, alachlor, butachlor, dimethachlor, dimethenamid, dimethenamid-P, metazachlor, metolachlor, S-metolachlor, pethoxamid, pretilachlor, propachlor, propisochlor and thenylchlor; acetamide-based ingredients such as diphenamid, napropamide and naproanilide; oxyacetamide-based ingredients such as flufenacet and mefenacet; tetrazolinone-based ingredients such as fentrazamide; and other ingredients that are said to exhibit herbicidal efficacies by inhibiting the microtubule polymerization, microtubule formation and cell division of plants or by inhibiting the biosynthesis of very long chain fatty acids (VLCFA), such as anilofos, indanofan, cafenstrole, piperophos, methiozolin, fenoxasulfone, pyroxasulfone and ipfencarbazone.

(k) Nitrile-based ingredients such as DBN (dichlobenil) and DCBN (chlorthiamid); benzamide-based ingredients such as isoxaben; triazolocarboxamide-based ingredients such as flupoxam; quinoline carboxylic acid-based ingredients such as quinclorac; and other ingredients that are said to exhibit herbicidal efficacies by inhibiting the cell wall (cellulose) synthesis such as triaziflam and indaziflam.

(l) Dinitrophenol-based ingredients such as DNOC, DNBP (dinoseb) and dinoterb; and other ingredients that are said to exhibit herbicidal efficacies by uncoupling (membrane disruption).

(m) Thiocarbamate-based ingredients such as butylate, hexylthiocarbam (cycloate), dimepiperate, EPTC, esprocarb, molinate, orbencarb, pebulate, prosulfocarb, benthiocarb (thiobencarb), tiocarbazil, triallate, vernolate and diallate; phosphorodithioate-based ingredients such as SAP (bensulide); benzofuran-based ingredients such as benfuresate and ethofumesate; chlorocarbonic acid-based ingredients such as TCA, DPA (dalapon) and tetrapion (flupropanate); and other ingredients that are said to exhibit herbicidal efficacies by inhibiting the lipid biosynthesis of plants.

(n) Phenoxycarboxylic acid-based ingredients such as clomeprop, 2,4-PA (2,4-D), 2,4-DB, dichlorprop, MCPA, MCPB and MCPP (mecoprop); benzoic acid-based ingredients such as chloramben, MDBA (dicamba) and TCBA (2,3,6-TBA); pyridinecarboxylic acid-based ingredients such as clopyralid, aminopyralid, fluroxypyr, picloram, triclopyr and halauxifen; quinoline carboxylic acid-based ingredients such as quinclorac and quinmerac; phthalamate semicarbazone-based ingredients such as NPA (naptalam) and diflufenzopyr; and other ingredients that are said to exhibit herbicidal efficacies by disturbing the hormone action of plants such as benazolin, diflufenzopyr, fluroxypyr, chlorflurenol, aminocyclopyrachlor, and DAS534.

(o) Arylaminopropionic acid-based ingredients such as flamprop-isopropyl; pyrazolium-based ingredients such as difenzoquat; organic arsenic-based ingredients such as DSMA and MSMA; and other herbicides such as bromobutide, chlorflurenol, cinmethylin, cumyluron, dazomet, daimuron, methyl-dymron, etobenzanid, fosamine, oxaziclomefone, oleic acid, pelargonic acid, pyributicarb, endothall, sodium chlorate, metam, quinoclamine, cyclopyrimorate, tridiphane and clacyfos.

Examples of the phytotoxicity reducing agent (safener) that can be used in the present invention include benoxacor, cloquintocet, cloquintocet-mexyl, cyometrinil, cyprosulfamide, dichlormid, dicyclonon, dietholate, fenchlorazole, fenchlorazole-ethyl, fenclorim, flurazole, fluxofenim, furilazole, isoxadifen, isoxadifen-ethyl, mefenpyr, mefenpyr-diethyl, mephenate, naphthalic anhydride and oxabetrinil.

EXAMPLES

Formulation Examples

Some examples of formulations regarding herbicides according to the present invention are described below, but the compounds of the present invention (active ingredient), the additives and the addition ratios are not limited to those detailed in these examples, and can be modified over a wide range. The term "parts" in the formulation examples indicates "parts by weight".

Formulation Example 1

| Wettable Powder | |
|---|---|
| Compound of the present invention | 20 parts |
| White carbon | 20 parts |
| Diatomaceous earth | 52 parts |
| Sodium alkylsulfate | 8 parts |

The components mentioned above were uniformly mixed and then finely pulverized to obtain a wettable powder containing 20% of the active ingredient.

Formulation Example 2

| Emulsifiable concentrate | |
| --- | --- |
| Compound of the present invention | 20 parts |
| Xylene | 55 parts |
| Dimethylformamide | 15 parts |
| Polyoxyethylene phenyl ether | 10 parts |

The components mentioned above were mixed and dissolved to obtain an emulsion containing 20% of the active ingredient.

Formulation Example 3

| Granules | |
| --- | --- |
| Compound of the present invention | 5 parts |
| Talc | 40 parts |
| Clay | 38 parts |
| Bentonite | 10 parts |
| Sodium alkylsulfate | 7 parts |

The components mentioned above were uniformly mixed, and then finely pulverized. Subsequently, the resulting product was granulated into a granular shape having a diameter ranging from 0.5 to 1.0 mm to obtain granules containing 5% of the active ingredient.

Next, Synthesis Examples are described below. However, it should be understood that the present invention is not limited to the Examples described below.

Example 1

Synthesis of 5-(1,1-dioxido-8-(trifluoromethyl)thiochroman-5-yl)-4-methoxy-2-methylpyridazin-3(2H)-one (Compound No. A-1)

(Step 1)

Synthesis of 3-(6-bromo-2-fluoro-3-(trifluoromethyl) phenyl) propionic acid

[Chem. 11]

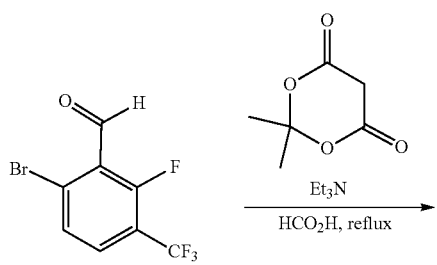

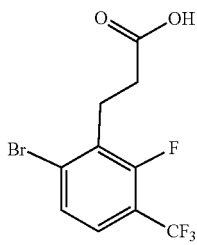

Formic acid (58.2 g), triethylamine (18.3 g), 6-bromo-2-fluoro-3-(trifluoromethyl)benzaldehyde (48.7 g), and Meldrum's acid (26.0 g) were successively placed at 0° C. in a four-necked flask with a volume of 500 mL. Subsequently, the mixture was heated to reflux for 4 hours.

Hydrochloric acid was added to the obtained solution, and a precipitated solid product was separated by filtration. The obtained solid product was dried. Thereby, 53.8 g of the target compound was obtained.

(Step 2)

Synthesis of 3-(6-bromo-2-fluooro-3-(trifluoromethyl) phenyl) propan-1-ol

[Chem. 12]

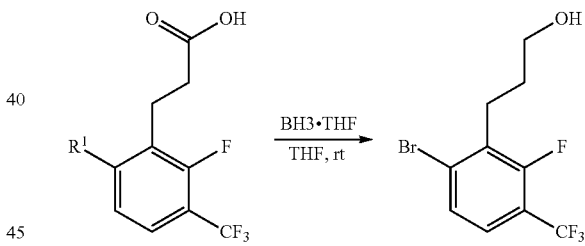

3-(6-Bromo-2-fluoro-3-(trifluoromethyl) phenyl) propionic acid (30 g) was dissolved in tetrahydrofuran (191 mL), and the solution was stirred at 0° C. A borane-tetrahydrofuran complex (0.9 M, 127 mL) was added thereto, and the mixture was stirred for one hour at room temperature.

The obtained solution was poured into hydrochloric acid, and subsequently, the mixture was subjected to extraction with ethyl acetate. The obtained organic layer was washed with a saturated aqueous solution of sodium chloride, dried over anhydrous magnesium sulfate, and subjected to filtration. The filtrate was concentrated under reduced pressure. The obtained residue was purified by column chromatography on silica gel. Thereby, 28.9 g of the target compound was obtained.

(Step 3)

Synthesis of 1-bromo-2-(3-chloropropyl)-3-fluoro-4-(trifluoromethyl) benzene

[Chem. 13]

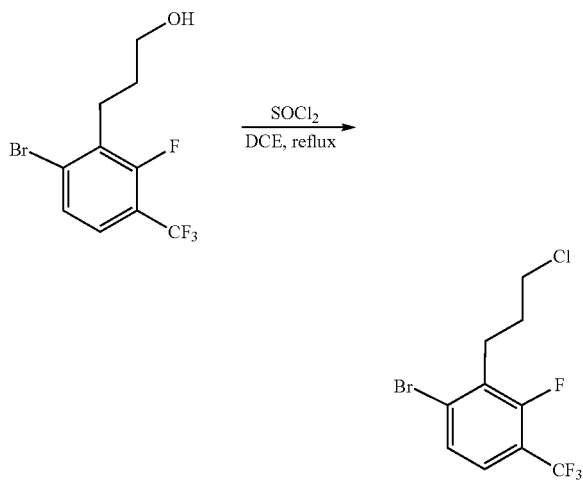

3-(6-Bromo-2-fluoro-3-(trifluoromethyl) phenyl) propan-1-ol (15.3 g) was dissolved in dichloroethane (102 mL), and the solution was stirred at room temperature. Thionyl chloride (9.1 g) and N,N-dimethylformamide (0.2 g) were added thereto, and the mixture was heated to reflux for 2 hours.

The obtained solution was concentrated under reduced pressure. The obtained residue was purified by column chromatography on silica gel. Thereby, 16.4 g of the target compound was obtained.

(Step 4)

Synthesis of 5-bromo-8-(trifluoromethyl) thiochroman

[Chem. 14]

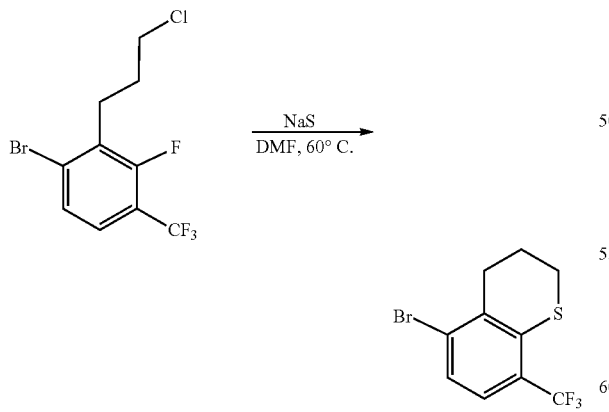

1-Bromo-2-(3-chloropropyl)-3-fluoro-4-(trifluoromethyl) benzene (14.4 g) was dissolved in N,N-dimethylformamide (158 mL), and the solution was stirred at room temperature. Sodium sulphide (4.2 g) was added thereto, and the mixture was heated at 60° C. overnight to reflux.

The obtained solution was poured into water, and subsequently subjected to extraction with ethyl acetate. The obtained organic layer was washed with a saturated aqueous solution of sodium chloride, dried over anhydrous magnesium sulfate, and subjected to filtration. The filtrate was concentrated under reduced pressure. The residue was purified by column chromatography on silica gel. Thereby, 6.8 g of the target compound was obtained.

(Step 5)

Synthesis of 5-bromo-8-(trifluoromethyl) thiochroman 1,1-dioxide

[Chem. 15]

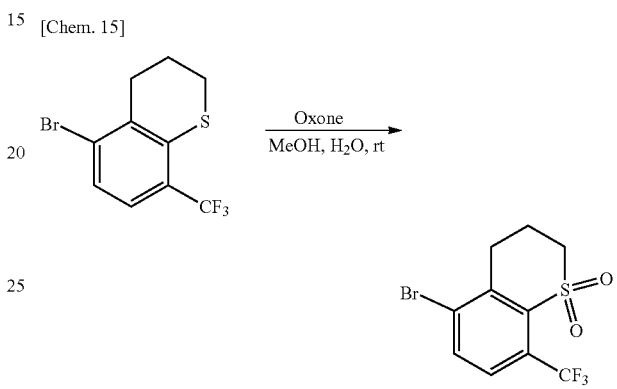

5-Bromo-8-(trifluoromethyl) thiochroman (2.0 g) was dissolved in 27 mL of methanol and 7 mL of water, and the solution was stirred at room temperature. Oxone (8.3 g) was added thereto, and the mixture was stirred for 48 hours at room temperature.

The resultant solution was subjected to filtration. The filtrate was concentrated under reduced pressure. Water was poured thereinto, and the mixture was subjected to extraction with ethyl acetate. The obtained organic layer was washed with a saturated aqueous solution of sodium chloride, dried over anhydrous magnesium sulfate, and subjected to filtration. The filtrate was concentrated under reduced pressure. The obtained residue was purified by column chromatography on silica gel. Thereby, 2.0 g of the target compound was obtained.

(Step 6)

Synthesis of 5-(1,1-dioxido-8-(trifluoromethyl) thiochroman-5-yl)-4-methoxy-2-methylpyridazin-3(2H)-one (Compound No.: A-1)

[Chem. 16]

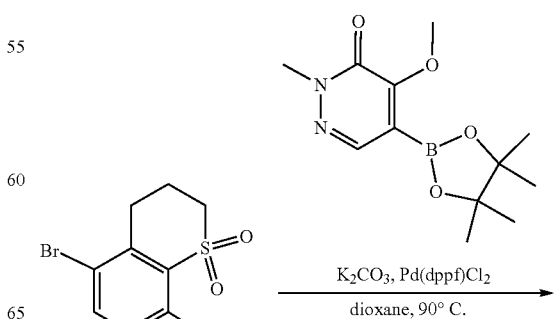

-continued

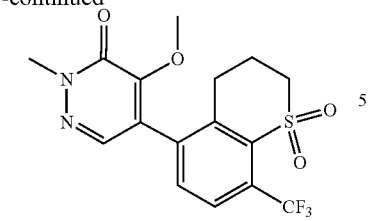

5-Bromo-8-(trifluoromethyl) thiochroman 1,1-dioxide (0.36 g) was dissolved in dioxane (10 mL), and the solution was stirred at room temperature. 4-Methoxy-2-methyl-5-(4,4,5,5-tetramethyl-1,3,2-dioxaboran-2-yl) pyridazin-3(2H)-one (0.27 g), potassium carbonate (0.41 g), and [1,1'-bis(diphenylphosphino) ferrocene] palladium (II) dichloride-dichloromethane adduct (0.04 g) were successively added thereto. The mixture was stirred overnight at 90° C.

The obtained solution was subjected to filtration. The filtrate was concentrated under reduced pressure. The obtained residue was purified by column chromatography on silica gel. Thereby, 0.22 g of the target compound was obtained.

Compound A-1: $^1$H-NMR (400 MHz, CDCl$_3$): δ 2.40-2.48 (m, 2H), 2.72-2.80 (m, 1H), 2.86-2.95 (m, 1H), 3.40 (t, 2H), 3.83 (s, 3H), 4.12 (s, 3H), 7.41 (d, 1H), 7.44 (s, 1H), 7.84 (d, 1H).

Example 2

Synthesis of 5-(1,1-dioxido-8-(trifluoromethyl) thiochroman-5-yl)-4-hydroxy-2-methylpyridazin-3(2H)-one (Compound No. A-2)

[Chem. 17]

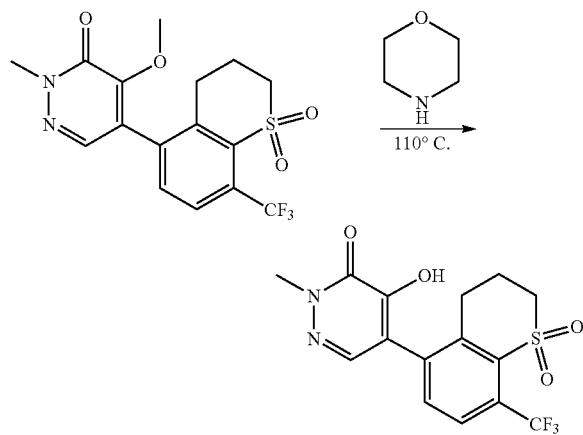

5-(1,1-Dioxido-8-(trifluoromethyl) thiochroman-5-yl)-4-methoxy-2-methylpyridazin-3(2H)-one (0.39 g) was dissolved in morpholine (2 mL). The solution was heated to 110° C. for one hour to reflux.

The obtained solution was poured into hydrochloric acid, and the mixture was subjected to extraction with ethyl acetate. The obtained organic layer was washed with a saturated aqueous solution of sodium chloride, dried over anhydrous magnesium sulfate, and subjected to filtration. The filtrate was concentrated under reduced pressure. Thereby, 0.31 g of the target compound.

Example 3

Synthesis of 1-((5-(1,1-dioxido-8-(trifluoromethyl) thiochroman-5-yl)-2-methyl-3-oxo-2,3-dihydropyridazin-4-yl) oxy) ethyl methyl carbonate (Compound No. A-3)

[Chem. 18]

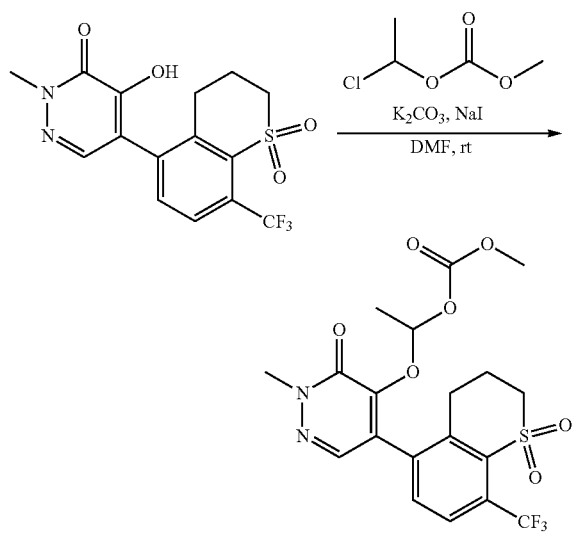

5-(1,1-dioxido-8-(trifluoromethyl) thiochroman-5-yl)-4-hydroxy-2-methylpyridazin-3(2H)-one (0.10 g) was dissolved in N,N-dimethylformamide (1 mL), and the solution was stirred at room temperature. Potassium carbonate (0.06 g), 1-chloroethyl methylcarbonate (0.06 g), and sodium iodide (0.01 g) were successively added thereto, and the mixture was stirred for 3 hours at room temperature.

The obtained solution was concentrated under reduced pressure. The obtained residue was purified by column chromatography on silica gel. Thereby, 0.11 g of the target compound was obtained.

Examples of the compounds of the present invention produced by the same methods as those described in the above Synthesis Examples are shown in Table 1. Table 1 indicates the substituents of the compounds represented by Formula (I-1). In addition, the melting point thereof is also described as physical data. In the table, Me indicates a methyl group, $^i$Pr indicates an i-propyl group, °Pr indicates a cyclopropyl group, and Ph indicates a phenyl group. The same meanings as described above are applied to Table 2.

[Chem. 19]

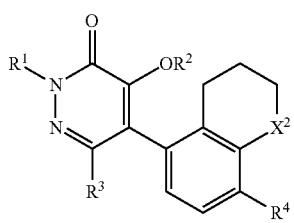

(I-1)

TABLE 1

| Compound No. | R¹ | R² | R³ | R⁴ | X² | Physical property |
|---|---|---|---|---|---|---|
| A-2 | Me | H | H | $CF_3$ | $SO_2$ | m.p. 287-288° C. |
| A-3 | Me | CH(Me)O—$CO_2$Me | H | $CF_3$ | $SO_2$ | m.p. 234-235° C. |
| A-4 | Me | H | H | CN | $SO_2$ | * |
| A-5 | MeOCH$_2$CH$_2$ | H | H | $CF_3$ | $SO_2$ | m.p. 279-280° C. |
| A-6 | Me | CO(1-Me-1H-pyrazol-4-yl) | H | $CF_3$ | $SO_2$ | m.p. 283-287° C. |
| A-7 | Me | CO(1,3-Me$_2$-1H-pyrazol-5-yl) | H | $CF_3$ | $SO_2$ | * |
| A-8 | Me | H | H | $CHF_2$ | $SO_2$ | m.p. 278-280° C. |
| A-9 | $CH_2$=CHCH$_2$ | H | H | $CF_3$ | $SO_2$ | m.p. 251-252° C. |
| A-10 | Me | CH(Me)O—$CO^i$Pr | H | $CF_3$ | $SO_2$ | m.p. 181-183° C. |
| A-11 | Me | $CH_2$O—$CO^i$Pr | H | $CF_3$ | $SO_2$ | m.p. 118-121° C. |
| A-12 | Me | $CH_2$(4-MeOPh) | H | $CF_3$ | $SO_2$ | m.p. 157-159° C. |
| A-13 | Me | $SO_2$(4-MePh) | H | $CF_3$ | $SO_2$ | m.p. 243-245° C. |
| A-14 | Me | $CO_2$Me | H | $CF_3$ | $SO_2$ | m.p. 237-239° C. |
| A-15 | Me | COMe | H | $CF_3$ | $SO_2$ | m.p. 226-229° C. |
| A-16 | Me | COPh | H | $CF_3$ | $SO_2$ | m.p. 265-268° C. |
| A-17 | $^c$Pr | H | H | $CF_3$ | $SO_2$ | m.p. 250-251° C. |
| A-18 | Me | H | H | Cl | S | * |
| A-19 | $CF_3CH_2$ | H | H | $CF_3$ | $SO_2$ | m.p. 279-280° C. |
| A-20 | Me | H | $^c$Pr | $CF_3$ | $SO_2$ | m.p. 299-300° C. |
| A-21 | Me | H | Me | $CF_3$ | $SO_2$ | m.p. 262-263° C. |
| A-22 | MeOCH$_2$ | H | H | $CF_3$ | $SO_2$ | m.p. 206-207° C. |
| A-23 | Me | CH(Me)O—$CO_2$Me | H | $CF_3$ | S | m.p. 140-141° C. |
| A-24 | Me | H | H | $CF_3$ | S | m.p. 246-249° C. |
| A-25 | Me | $CH_2CH_2$OMe | H | $CF_3$ | $SO_2$ | m.p. 135-137° C. |
| A-26 | Me | H | H | $OCHF_2$ | $SO_2$ | m.p. 294-296° C. |
| A-27 | Me | H | H | $OCF_3$ | $SO_2$ | m.p. 262-263° C. |

In addition, examples of the compounds of the present invention produced in the same methods as described above are shown in Table 2.

TABLE 2

| Compound No. | Structural formula | Physical property |
|---|---|---|
| B-1 | | * |
| B-2 | | m.p. 216-218° C. |
| B-3 | | m.p. 238-240° C. |
| B-4 |  | * |

Among the compounds described in Tables 1 and 2, each compound having * in the cell of the physical property was in an amorphous condition or in a form of a viscous oil. The ¹H-NMR data thereof are described below.

Compound A-4: ¹H-NMR (400 MHz, DMSO d-6): δ 2.20-2.26 (m, 2H), 2.78-2.79 (m, 2H), 3.68-3.72 (m, 5H), 7.65 (d, 1H), 7.70 (s, 1H), 8.07 (d, 1H).

Compound A-7: ¹H-NMR (400 MHz, CDCl$_3$): δ 2.25 (s, 3H), 2.46-2.52 (m, 2H), 2.90-2.96 (m, 2H), 3.40-3.43 (m, 2H), 3.91 (s, 3H), 4.06 (s, 3H), 6.63 (s, 1H), 7.51 (d, 1H), 7.64 (s, 1H), 7.86 (d, 1H).

Compound A-18: ¹H-NMR (400 MHz, CDCl$_3$): δ 2.05-2.17 (m, 2H), 2.64 (m, 2H), 3.06-3.08 (m, 2H), 3.88 (s, 3H), 6.87 (d, 1H), 7.28 (d, 1H), 7.61 (s, 1H).

Compound B-1: ¹H-NMR (400 MHz, DMSO d-6): δ 2.30-2.36 (m, 2H), 3.16-3.19 (m, 2H), 3.50-3.58 (m, 2H), 3.70 (s, 3H), 7.47 (d, 1H), 7.62 (s, 1H), 8.01 (d, 1H).

Compound B-4: ¹H-NMR (400 MHz, DMSO d-6): δ 2.21-2.28 (m, 2H), 2.76-2.81 (m, 2H), 3.54-3.56 (m, 2H), 3.72 (s, 3H), 7.77 (d, 1H).

(Evaluation of Herbicidal Effects)

Next, it is demonstrated in the Test Examples described below that the compounds according to the present invention are useful as an active ingredient of a herbicide.

Test Example 1

(1) Preparation of an Emulsifiable Concentrate for Test

An emulsifiable concentrate was prepared by mixing and dissolving POE allyl phenyl ether (4.1 parts by weight), POE-POP glycol (1 part by weight), POE sorbitan laurate (0.8 parts by weight), glycerin (2.6 parts by weight), dimethylformamide (65.9 parts by weight), N-methylpyrrolidone (5.1 parts by weight), cyclohexanone (15.4 parts by weight), and aromatic hydrocarbon (5.1 parts by weight). A compound of the present invention (4 mg) was dissolved in the obtained emulsifiable concentrate (100 μm) to prepare an emulsifiable concentrate for test. POA means "polyoxyalkylene", POE means "polyoxyethylene", and POP means "polyoxypropylene".

(2) Treatment of Spraying onto Shoots

Seeds of each of *Avena sativa, Matricaria chamomilla, Setaria faberi, Digitaria ciliaris, Abutilon theophrasti,* and *Amaranthus retroflexus* were placed in a surface layer of soil filled in a pot with a size of 150 cm$^2$ and then lightly covered with soil. Subsequently, the pots were kept in a greenhouse to allow the plants to grow. When each of the plants grew to a shoot height ranging from 2 to 4 cm, the emulsifiable concentrate mentioned above was diluted with water so as to have a specified amount of the active ingredient, and then sprayed onto the shoot parts by means of a small-sized sprayer at an application rate of 250 L of water per hectare.

(3) Evaluation

Three weeks after the treatment, the weight of the shoot part of the alive plant in the untreated plot and the treated plot with respect to each of the weeds was measured. The herbicidal index was calculated according to the calculation expression described below.

(4) Calculation Expression for Herbicidal Index

Herbicidal index (%)=[(Weight of the shoot part of the alive plant in the untreated plot−Weight of the shoot part of the alive plant in the treated plot)/(Weight of the shoot part of the alive plant in the untreated plot)]×100

(a) *Avena sativa*

A diluted emulsifiable concentrate of each of the compounds shown in Table 3 was sprayed at a dosage of 250 g of the compound per hectare. As a result, all the compounds exhibited 100% of the herbicidal activity with respect to *Avena sativa*.

TABLE 3

| Compound No. |
| --- |
| A-2 |
| A-3 |
| A-5 |
| A-6 |
| A-7 |
| A-10 |
| A-11 |
| A-12 |
| A-13 |
| A-14 |
| A-15 |
| A-16 |
| A-17 |
| A-18 |
| A-19 |
| A-20 |
| A-21 |
| A-22 |
| A-23 |
| A-24 |

TABLE 3-continued

| Compound No. |
| --- |
| B-1 |
| B-2 |

(b) *Matricaria chamomilla*

A diluted emulsifiable concentrate of each of the compounds shown in Table 4 was sprayed at a dosage of 250 g of the compound per hectare. As a result, all the compounds exhibited 80% or more of the herbicidal activity with respect to *Matricaria chamomilla*.

TABLE 4

| Compound No. |
| --- |
| A-2 |
| A-3 |
| A-4 |
| A-5 |
| A-6 |
| A-7 |
| A-8 |
| A-9 |
| A-10 |
| A-11 |
| A-12 |
| A-13 |
| A-14 |
| A-15 |
| A-16 |
| A-17 |
| A-18 |
| A-19 |
| A-20 |
| A-21 |
| A-22 |
| A-23 |
| A-24 |
| B-1 |
| B-2 |
| B-3 |
| A-27 |
| B-4 |

(c) *Setaria faberi*

A diluted emulsifiable concentrate of each of the compounds shown in Table 5 was sprayed at a dosage of 250 g of the compound per hectare. As a result, all the compounds exhibited 100% of the herbicidal activity with respect to *Setaria faberi*.

TABLE 5

| Compound No. |
| --- |
| A-2 |
| A-3 |
| A-4 |
| A-5 |
| A-6 |
| A-7 |
| A-8 |
| A-10 |
| A-11 |
| A-12 |
| A-13 |
| A-14 |
| A-15 |
| A-16 |
| A-18 |
| A-20 |
| A-21 |
| A-22 |

TABLE 5-continued

| Compound No. |
| --- |
| A-23 |
| A-24 |
| B-1 |
| B-2 |
| B-3 |

(d) *Digitaria ciliaris*

A diluted emulsifiable concentrate of each of the compounds shown in Table 6 was sprayed at a dosage of 250 g of the compound per hectare. As a result, all the compounds exhibited 100% of the herbicidal activity with respect to *Digitaria ciliaris*.

TABLE 6

| Compound No. |
| --- |
| A-2 |
| A-3 |
| A-4 |
| A-5 |
| A-6 |
| A-7 |
| A-8 |
| A-9 |
| A-10 |
| A-11 |
| A-12 |
| A-13 |
| A-14 |
| A-15 |
| A-16 |
| A-17 |
| A-18 |
| A-19 |
| A-20 |
| A-21 |
| A-22 |
| A-23 |
| A-24 |
| B-1 |
| B-2 |
| B-3 |
| A-26 |

(e) *Abutilon theophrasti*

A diluted emulsifiable concentrate of each of the compounds shown in Table 7 was sprayed at a dosage of 250 g of the compound per hectare. As a result, all the compounds exhibited 80% or more of the herbicidal activity with respect to *Abutilon theophrasti*.

TABLE 7

| Compound No. |
| --- |
| A-2 |
| A-3 |
| A-5 |
| A-6 |
| A-7 |
| A-8 |
| A-9 |
| A-10 |
| A-11 |
| A-12 |
| A-13 |
| A-14 |
| A-15 |
| A-16 |
| A-17 |
| A-18 |

TABLE 7-continued

| Compound No. |
| --- |
| A-20 |
| A-21 |
| A-22 |
| A-23 |
| A-24 |
| B-1 |
| B-3 |
| A-4 |
| A-25 |
| A-26 |
| A-27 |

(f) *Amaranthus retroflexus*

A diluted emulsifiable concentrate of each of the compounds shown in Table 8 was sprayed at a dosage of 250 g of the compound per hectare. As a result, all the compounds exhibited 100% of the herbicidal activity with respect to *Amaranthus retroflexus*.

TABLE 8

| Compound No. |
| --- |
| A-2 |
| A-3 |
| A-4 |
| A-5 |
| A-6 |
| A-7 |
| A-8 |
| A-9 |
| A-10 |
| A-11 |
| A-12 |
| A-13 |
| A-14 |
| A-15 |
| A-16 |
| A-17 |
| A-18 |
| A-19 |
| A-20 |
| A-21 |
| A-22 |
| A-23 |
| A-24 |
| B-1 |
| B-2 |
| B-3 |

Test Example 2

Tests of Treating Shoots (1) Preparation of an Emulsifiable Concentrate for Test An emulsifiable concentrate for test was prepared in the same manner as that described in Test Example 1.

(2) Treatment of Spraying onto Shoots

Seeds of each of *Lolium multiflorum*, *Digitaria ciliaris*, and *Zea mays* for feed were placed in a surface layer of soil filled in a pot with a size of 150 cm$^2$ and then lightly covered with soil. Subsequently, the pots were kept in a greenhouse to allow the plants to grow. When each of *Lolium multiflorum* and *Digitaria ciliaris* grew to a shoot height ranging from 2 to 4 cm, and *Zea mays* for feed grew to a shoot height ranging from 20 to 30 cm, the emulsifiable concentrate mentioned above was diluted with water so as to have a specified amount of the active ingredient, and then sprayed onto the shoot parts by means of a small-sized sprayer at an application rate of 250 L of water per hectare.

(3) Evaluation

Four weeks after the treatment, the weight of the shoot part of the alive plant in the untreated plot and the treated plot with respect to each of *Lolium multiflorum*, *Digitaria ciliaris*, and *Zea mays* for feed was measured. The herbicidal index was calculated according to the calculation expression described below.

(4) Calculation Expression for Herbicidal Index

Herbicidal index (%)=[(Weight of the shoot part of the alive plant in the untreated plot−Weight of the shoot part of the alive plant in the treated plot)/(Weight of the shoot part of the alive plant in the untreated plot)]×100

A diluted emulsifiable concentrate of the compound of A-2 was sprayed at a dosage of 63 g of the compound per hectare.

In addition, with respect to the compound (A) described in Patent Document 1, the same application as described above was carried out.

[Chem. 20]

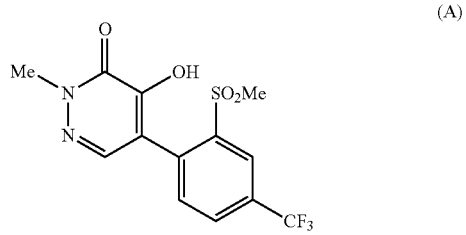

(A)

The herbicidal index of each of the compounds is shown in Table 9.

TABLE 9

| Compound No. | Dosage | Herbicidal index | | |
| --- | --- | --- | --- | --- |
| | | *Lolium multiflorum* | *Digitaria ciliaris* | *Zea mays* for feed |
| A-2 | 63 g/ha | 100% | 90% | 0% |
| (A) | 63 g/ha | 40% | 80% | 50% |

Test Example 3

(1) Preparation of an Emulsifiable Concentrate for Test

An emulsifiable concentrate for test was prepared in the same manner as that described in Test Example 1.

(2) Treatment of Spraying onto Shoots

Seeds of each of *Zea mays* for feed, *Alopecurus myosuroides*, *Lolium multiflorum*, *Avena sativa*, *Digitaria ciliaris*, *Setaria faberi*, *Abutilon theophrasti*, and *Amaranthus retroflexus* were placed in a surface layer of soil filled in a pot with a size of 150 cm$^2$ and then lightly covered with soil. Subsequently, the pots were kept in a greenhouse to allow the plants to grow. When each of *Alopecurus myosuroides*, *Lolium multiflorum*, *Avena sativa*, *Digitaria ciliaris*, *Setaria faberi*, *Abutilon theophrasti*, and *Amaranthus retroflexus* grew to a shoot height ranging from 2 to 4 cm, and *Zea mays* for feed grew to a shoot height ranging from 20 to 30 cm, the emulsifiable concentrate mentioned above was diluted with water so as to have a specified amount of the active ingredient, and then sprayed onto the shoot parts by means of a small-sized sprayer at an application rate of 250 L of water per hectare.

(3) Evaluation

Three weeks after the treatment, the weight of the shoot part of the alive plant in the untreated plot and the treated plot with respect to each plant was measured. The herbicidal index was calculated according to the calculation expression described below.

(4) Calculation Expression for Herbicidal Index

Herbicidal index (%)=[(Weight of the shoot part of the alive plant in the untreated plot−Weight of the shoot part of the alive plant in the treated plot)/(Weight of the shoot part of the alive plant in the untreated plot)]×100

A diluted emulsifiable concentrate of the compound of A-2 was sprayed at a dosage of 250 g or 63 g of the compound per hectare.

In addition, with respect to the compound (A) described in Patent Document 1, the same application as described above was carried out.

The herbicidal index of each of the compounds is shown in Table 10. In Table 10, "g ai" indicates gram (g) of the active ingredient.

TABLE 10

| Compound | Application amount | Herbicidal index | | | | | | | |
| --- | --- | --- | --- | --- | --- | --- | --- | --- | --- |
| | | *Alopecurus myosuroides* | *Lolium multiflorum* | *Avena sativa* | *Digitaria ciliaris* | *Setaria faberi* | *Abutilon theophrasti* | *Amaranthus retroflexus* | *Zea mays* for feed |
| A-2 | 250 g ai/ha | 100% | 100% | 100% | 100% | 100% | 100% | 100% | 20% |
| A-2 | 63 g ai/ha | 80% | 100% | 100% | 90% | 100% | 100% | 100% | 0% |
| (A) | 250 g ai/ha | 90% | 50% | 80% | 90% | 100% | 90% | 100% | 90% |
| (A) | 63 g ai/ha | 50% | 40% | 60% | 80% | 80% | 80% | 100% | 40% |

As is clear from the results shown in Table 9 and Table 10 mentioned above, the compound of the present invention exhibits superior herbicidal effects in the treatments on the shoots even at a lower dosage, as compared with the compound described in Patent Document 1. On the other hand, the compound of the present invention did not exhibit herbicidal effects on Zea mays for feed, and for this reason, it can be seen that the compound of the present invention is safer with respect to crops.

INDUSTRIAL APPLICABILITY

The pyridazine compounds of the present invention exhibit a reliable effect of controlling weeds even at a low dosage, have less phytotoxicity to crops, and are highly safe for the environment. For this reason, the pyridazine compounds of the present invention are useful as an active ingredient of herbicides. The herbicides of the present invention can be safely used for controlling weeds in the cultivation of agricultural and horticultural crops.

What is claimed is:

1. A compound represented by formula (I) or a salt thereof:

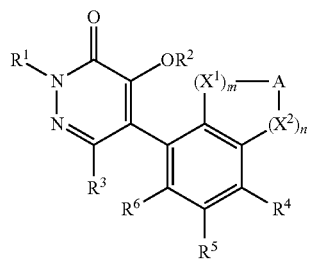

wherein:
$R^1$ represents a substituted or unsubstituted C1 to C6 alkyl group, a substituted or unsubstituted C2 to C6 alkenyl group, a substituted or unsubstituted C2 to C6 alkynyl group, or a substituted or unsubstituted C3 to C6 cycloalkyl group, $R^2$ represents a hydrogen atom, a substituted or unsubstituted C1 to C6 alkyl group, a substituted or unsubstituted C2 to C6 alkenyl group, a substituted or unsubstituted C2 to C6 alkynyl group, a group represented by $R^a$—CO—, a group represented by $R^aO$—CO—, a group represented by $R^aNH$—CO—, a group represented by $R^a_2N$—CO—, a group represented by $R^a$—SO$_2$—, a group represented by $R^a$—CO—O—CR$^b_2$—, or a group represented by $R^a$ O—CO—O—CR$^b_2$—, each $R^a$ independently represents a substituted or unsubstituted C1 to C6 alkyl group, a substituted or unsubstituted C2 to C6 alkenyl group, a substituted or unsubstituted C2 to C6 alkynyl group, a substituted or unsubstituted C3 to C6 cycloalkyl group, a substituted or unsubstituted phenyl group, a substituted or unsubstituted naphthyl group, or a substituted or unsubstituted 5- to 6-membered heterocyclyl group, each $R^b$ independently represents a hydrogen atom, or a substituted or unsubstituted C1 to C6 alkyl group, $R^3$ represents a hydrogen atom, a substituted or unsubstituted C1 to C6 alkyl group, a substituted or unsubstituted C2 to C6 alkenyl group, a substituted or unsubstituted C2 to C6 alkynyl group, or a substituted or unsubstituted C3 to C6 cycloalkyl group, $R^4$ represents a halogeno group, a substituted or unsubstituted C1 to C6 alkyl group, a substituted or unsubstituted C1 to C6 alkoxy group, a substituted or unsubstituted phenyl group, a substituted or unsubstituted naphthyl group, a substituted or unsubstituted 5- to 6-membered heteroaryl group, or a cyano group, $R^5$ represents a hydrogen atom, or a halogeno group, $R^6$ represents a hydrogen atom, or a halogeno group, A represents a substituted or unsubstituted C1 to C4 alkylene group, a substituted or unsubstituted C2 to C3 alkenylene group, or a substituted or unsubstituted C1 to C2 alkyleneoxy C1 to C2 alkylene group, $X^1$ represents an oxygen atom, or a sulfonyl group, $X^2$ represents an oxygen atom, a sulfenyl group, a sulfinyl group, a sulfonyl group, a group represented by —S(=NR$^c$)—, or a group represented by —S(=O)(=NR$^c$)—, each $R^c$ independently represents a hydrogen atom, a substituted or unsubstituted C1 to C6 alkyl group, a substituted or unsubstituted phenyl group, a substituted or unsubstituted naphthyl group, or a cyano group, m represents 0 or 1, n represents 0 or 1, and the sum of m and n is 1 or 2, and when A is a substituted or unsubstituted methylene group, the sum of m and n is 2.

2. A herbicide containing at least one selected from the group consisting of the compounds as recited in claim 1 and salts thereof, as an active ingredient.

3. A method for controlling weeds of monocotyledonous species and/or dicotyledonous species in useful plants, comprising the step of applying the compound as recited in claim 1 or a salt thereof to said weeds and/or said plants and/or locuses thereof.

4. A method for controlling weeds of monocotyledonous species and/or dicotyledonous species in useful plants, comprising the step of applying the herbicide as recited in claim 2 to said weeds and/or said plants and/or locuses thereof.

* * * * *